(12) United States Patent
Yerkes et al.

(10) Patent No.: US 8,906,826 B2
(45) Date of Patent: Dec. 9, 2014

(54) HERBICIDAL COMPOSITIONS COMPRISING 4-AMINO-3-CHLORO-5-FLUORO-6-(4-CHLORO-2-FLUORO-3-METHOXYPHENYL) PYRIDINE-2-CARBOXYLIC ACID OR A DERIVATIVE THEREOF AND IMIDAZOLINONES

(71) Applicant: Dow AgroSciences, LLC, Indianapolis, IN (US)

(72) Inventors: Carla N. Yerkes, Crawfordsville, IN (US); Richard K. Mann, Franklin, IN (US); Paul R. Schmitzer, Indianapolis, IN (US); Norbert M. Satchivi, Westfield, IN (US)

(73) Assignee: Dow AgroSciences, LLC., Indianapolis, IN (US)

( * ) Notice: Subject to any disclaimer, the term of this patent is extended or adjusted under 35 U.S.C. 154(b) by 0 days.

(21) Appl. No.: 13/833,659

(22) Filed: Mar. 15, 2013

(65) Prior Publication Data

US 2014/0031213 A1     Jan. 30, 2014

Related U.S. Application Data

(60) Provisional application No. 61/675,043, filed on Jul. 24, 2012.

(51) Int. Cl.
| | | |
|---|---|---|
| A01N 25/26 | (2006.01) | |
| A01N 43/40 | (2006.01) | |
| A01N 43/54 | (2006.01) | |

(52) U.S. Cl.
CPC ............... *A01N 43/40* (2013.01); *A01N 43/54* (2013.01)
USPC .......................................... 504/100; 504/130

(58) Field of Classification Search
None
See application file for complete search history.

(56) References Cited

U.S. PATENT DOCUMENTS

| | | |
|---|---|---|
| 7,314,849 B2 | 1/2008 | Balko et al. |
| 7,622,641 B2 | 11/2009 | McCutchen et al. |
| 2009/0062121 A1 | 3/2009 | Satchivi et al. |
| 2010/0137137 A1 | 6/2010 | Rosinger et al. |
| 2011/0082162 A1 | 4/2011 | Lorsbach et al. |
| 2011/0207607 A1 | 8/2011 | Satchivi et al. |
| 2012/0115727 A1 | 5/2012 | Satchivi et al. |
| 2012/0190551 A1 | 7/2012 | Yerkes et al. |
| 2013/0109569 A1 | 5/2013 | Dave et al. |
| 2013/0310256 A1 | 11/2013 | Yerkes et al. |
| 2014/0031210 A1 | 1/2014 | Yerkes et al. |
| 2014/0031211 A1 | 1/2014 | Yerkes et al. |
| 2014/0031212 A1 | 1/2014 | Yerkes et al. |
| 2014/0031214 A1 | 1/2014 | Yerkes et al. |
| 2014/0031215 A1 | 1/2014 | Yerkes et al. |
| 2014/0031216 A1 | 1/2014 | Yerkes et al. |
| 2014/0031217 A1 | 1/2014 | Yerkes et al. |
| 2014/0031218 A1 | 1/2014 | Mann et al. |
| 2014/0031219 A1 | 1/2014 | Yerkes et al. |
| 2014/0031220 A1 | 1/2014 | Yerkes et al. |
| 2014/0031221 A1 | 1/2014 | Yerkes et al. |
| 2014/0031222 A1 | 1/2014 | Yerkes et al. |
| 2014/0031227 A1 | 1/2014 | Yerkes et al. |
| 2014/0031228 A1 | 1/2014 | Mann et al. |
| 2014/0031229 A1 | 1/2014 | Mann et al. |

FOREIGN PATENT DOCUMENTS

WO    WO 2007/082098     7/2007

OTHER PUBLICATIONS

Thomas, S., Written Opinion of the International Search Authority for PCT/US2013/051294, Nov. 27, 2013, pp. 1-5, ISA/US.
Thomas, S., International Search Report for PCT/US2013/051294, Nov. 27, 2013, pp. 1-4, ISA/US.
Synthesis of Esters: Esterification Reactions, obtained via google.com in U.S. Appl. No. 13/840,306, obtained online Mar. 8, 2014.
Chui, M.P., Non-Final Office Action in U.S. Appl. No. 13/840,306, Mar. 13, 2014, pp. 1-12, USPTO.
Pryor, A.N., Notice of Allowance and Fee(s) Due for U.S. Appl. No. 13/832,978, Apr. 9, 2014, pp. 1-13, USPTO.
Pryor, A.N., Notice of Allowance and Fee(s) Due for U.S. Appl. No. 13/833,315, May 12, 2014, pp. 1-8, USPTO.
Pryor, S.N., Notice of Allowance and Fee(s) Due for U.S. Appl. No. 13/833,315, Mar. 20, 2014, pp. 1-11, USPTO.

(Continued)

*Primary Examiner* — Alton Pryor
(74) *Attorney, Agent, or Firm* — Michael R. Asam; Faegre Baker Daniels LLP.

(57) ABSTRACT

A synergistic herbicidal composition containing (a) a compound of formula (I):

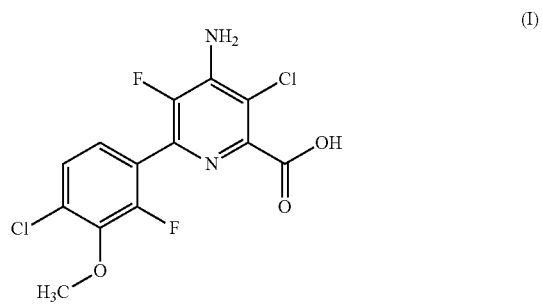

or an agriculturally acceptable salt or ester thereof and (b) an imidazolinone, including but not limited to imazethapyr ammonium, imazamox ammonium, imazapic ammonium, imazapyr isopropylamine salt, imazamethabenz-methyl and imazaquin isopropylamine salt, provide control of undesirable vegetation e.g., in direct-seeded rice, water-seeded rice, transplanted rice, cereals, wheat, barley, oats, rye, sorghum, corn or maize, sugarcane, sunflower, oilseed rape, canola, sugar beet, soybean, cotton, pineapple, vegetables, pastures, grasslands, rangelands, fallowland, turf, tree and vine orchards, aquatics, plantation crops, vegetables, industrial vegetation management (IVM) and rights of way (ROW).

19 Claims, No Drawings

(56) References Cited

OTHER PUBLICATIONS

Pryor, A.N., Notice of Allowance and Fee(s) Due for U.S. Appl. No. 13/833,362, May 29, 2014, pp. 1-8, USPTO.
Pryor, A.N., Notice of Allowance and Fee(s) Due for U.S. Appl. No. 13/834,706, May 15, 2014, pp. 1-13, USPTO.
Pryor, A.N., Notice of Allowance and Fee(s) Due for U.S. Appl. No. 13/833,372, May 14, 2014, pp. 1-8, USPTO.
Pryor, A.N., Notice of Allowance and Fee(s) Due for U.S. Appl. No. 13/833,923, May 2, 2014, pp. 1-9, USPTO.
Pryor, A.N., Notice of Allowance and Fee(s) Due for U.S. Appl. No. 13/833,965, Apr. 1, 2014, pp. 1-8, USPTO.
Pryor, A.N., Notice of Allowance and Fee(s) Due for U.S. Appl. No. 13/834,326, May 13, 2014, pp. 1-4, USPTO.
Pryor, A.N., Notice of Allowance and Fee(s) Due for U.S. Appl. No. 13/834,326, Apr. 2, 2014, pp. 1-9, USPTO.
Pryor, A.N., Notice of Allowance and Fee(s) Due for U.S. Appl. No. 13/836,653, Apr. 2, 2014, pp. 1-8, USPTO.
Pryor, A.N., Notice of Allowance and Fee(s) Due for U.S. Appl. No. 13/837,990, Apr. 1, 2014, pp. 1-8, USPTO.
Pryor, A.N., Notice of Allowance and Fee(s) Due for U.S. Appl. No. 13/839,043, May 27, 2014, pp. 1-5, USPTO.
Pryor, A.N., Notice of Allowance and Fee(s) Due for U.S. Appl. No. 13/839,043, Mar. 24, 2014, pp. 1-8, USPTO.
Pryor, A.N., Notice of Allowance and Fee(s) Due for U.S. Appl. No. 13/840,236, Apr. 25, 2014, pp. 1-8, USPTO.
Pryor, A.N., Notice of Allowance and Fee(s) Due for U.S. Appl. No. 13/840,303, Apr. 25, 2014, pp. 1-8, USPTO.
Pryor, A.N., Notice of Allowance and Fee(s) Due for U.S. Appl. No. 13/840,346, Jun. 4, 2014, pp. 1-8, USPTO.
Pryor, A.N., Notice of Allowance and Fee(s) Due for U.S. Appl. No. 13/840,419, May 5, 2014, pp. 1-8, USPTO.
Pryor, A.N., Notice of Allowance and Fee(s) Due for U.S. Appl. No. 13/840,488, May 2, 2014, pp. 1-8, USPTO.

HERBICIDAL COMPOSITIONS COMPRISING 4-AMINO-3-CHLORO-5-FLUORO-6-(4-CHLORO-2-FLUORO-3-METHOXYPHENYL) PYRIDINE-2-CARBOXYLIC ACID OR A DERIVATIVE THEREOF AND IMIDAZOLINONES

PRIORITY CLAIM

This patent application claims the benefit of U.S. provisional patent application No. 61/675,043, filed on Jul. 24, 2012, which is incorporated herein by reference in its entirety.

FIELD

Provided herein are herbicidal compositions comprising (a) 4-amino-3-chloro-5-fluoro-6-(4-chloro-2-fluoro-3-methoxyphenyl) pyridine-2-carboxylic acid or an agriculturally acceptable ester or salt thereof and (b) imidazolinones. Provided herein are also methods of controlling undesirable vegetation comprising applying (a) 4-amino-3-chloro-5-fluoro-6-(4-chloro-2-fluoro-3-methoxyphenyl) pyridine-2-carboxylic acid or an agriculturally acceptable ester or salt thereof and (b) imidazolinones.

BACKGROUND

The protection of crops from weeds and other vegetation which inhibit crop growth is a constantly recurring problem in agriculture. To help combat this problem, researchers in the field of synthetic chemistry have produced an extensive variety of chemicals and chemical formulations effective in the control of such unwanted growth. Chemical herbicides of many types have been disclosed in the literature and a large number are in commercial use. However, there remains a need for compositions and methods that are effective in controlling undesirable vegetation.

SUMMARY

A first embodiment of the invention provided herein includes herbicidal compositions comprising an herbicidally effective amount of (a) a compound of the formula (I)

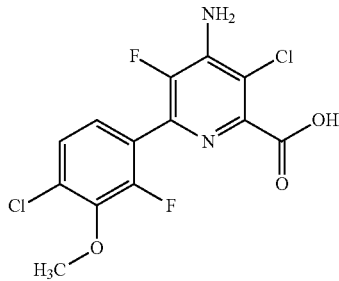

(I)

or an agriculturally acceptable salt or ester thereof, and (b) at least one imidazolinone.

A second embodiment includes the mixture of the first embodiment in which formula (I), is present in at least one of the following forms: a carboxylic acid, a carboxylate salt, an aralkyl, an alkyl ester, an unsubstituted benzyl, a substituted benzyl, a $C_{1-4}$ alkyl, and/or an n-butyl ester.

A third embodiment includes the mixture according to the first or second embodiments wherein the imidazolinone (b) is at least one compound selected from the group consisting of: imazethapyr, imazethapyr ammonium, imazamox, imazamox ammonium, imazapic, imazapic ammonium, imazapyr, imazapyr isopropylamine salt, imazamethabenz, imazamethabenz-methyl, imazaquin or imazaquin isopropylamine salt or an agriculturally acceptable salt or ester thereof.

A fourth embodiment includes the mixtures according to the first, second, or third embodiments in which the imidazolinone in the mixture is imazethapyr wherein the weight ratio of the compound of formula (I) to imazethapyr given in units of gae/ha to gai/ha or gae/ha to gae/ha is selected from the group of ranges of ratios and ratios consisting of: from about 1:70 to about 29:1, about 1:1, about 2:1, about 4:1.

A fifth embodiment includes the mixtures according to the first, second, or third embodiments in which the imidazolinone in the mixture is imazamox wherein the weight ratio of the compound of formula (I) to imazamox given in units of gae/ha to gai/ha or gae/ha to gae/ha is selected from the group of ranges of ratios and ratios consisting of: from about 1:35 to 45:1, about 1:1, about 1:1.3, about 1:26, about 1:5.1 to about 1:2.6; about 1:2.3 to about 1:6.1, about 1:3.2 to about 0.8:1, about 1:0.6.

A sixth embodiment includes the mixtures according to the first, second, or third embodiments in which the imidazolinone in the mixture is imazapic wherein the weight ratio of the compound of formula (I) to imazapic given in units of gae/ha to gai/ha or gae/ha to gae/ha is selected from the group of ranges of ratios and ratios consisting of: about 1:105 to about 5:1, about 1:1, about 2:1, about 1:2 to about 1:4, about 4:1, about 1:1.2, about 1:1.5, and about 1:8 to about 4.4:1.

A seventh embodiment includes the mixtures according to the first, second, or third embodiments in which the imidazolinone in the mixture is imazapyr wherein the weight ratio of the compound of formula (I) to imazapyr given in units of gae/ha to gai/ha or gae/ha to gae/ha is selected from the group of ranges of ratios and ratios consisting of: about 1.35:1, about 1.5:1, about 1:1, about 2:1, about 4:1, about 1:2, about 1:6.6, about 1:1.7, about 1:19.1, about 1:3.3, about 1:3.3, about 1:4, and about 1:8.

An eighth embodiment includes the mixtures according to the first, second, or third embodiments in which the imidazolinone in the mixture is imazamethabenz-methyl wherein the weight ratio of the compound of formula (I) to imazamethabenz-methyl given in units of gae/ha to gai/ha or gae/ha to gae/ha is selected from the group of ranges of ratios and ratios consisting of: about 1:350 to about 1.5:1, about 1:5.5, about 1:1, about 1:22, about 1:100, and about 1:50.

A ninth embodiment includes the mixtures according to the first, second, or third embodiments in which the imidazolinone in the mixture is imazaquin wherein the weight ratio of the compound of formula (I) to imazaquin given in units of gae/ha to gai/ha or gae/ha to gae/ha is selected from the group of ranges of ratios and ratios consisting of: about 1:105 to about 8:1, about 1:2.1, about 1:1, about 2:1, about 4:1.1, about 2:1.1, about 1:8.2, about 4.1:1, about 1:1.2, about 1:1.5, about 1:2, about 1:4, and about 1:2.

A tenth embodiment includes any composition according to the first through the ninth embodiments wherein the mixture further comprises at least one an agriculturally acceptable agent selected from the group consisting of an adjuvant, a carrier, or a safener.

An eleventh embodiment includes methods of controlling undesirable vegetation comprising the step of applying or otherwise contacting vegetation and/or soil, and/or water with an herbicidally effective amount of at least one mixture according to the first through the tenth embodiments.

A twelfth embodiment includes methods according to the eleventh embodiment wherein the method is practiced in at least one member of the group consisting of: direct-seeded, water-seeded, and/or transplanted rice, cereals, wheat, barley, oats, rye, sorghum, corn/maize, sugarcane, sunflower, oilseed rape, canola, sugar beet, soybean, cotton, pineapple, pastures, grasslands, rangelands, fallowland, turf, tree and vine orchards, aquatics, plantation crops, vegetables, industrial vegetation management (IVM), or rights-of-way (ROW).

A thirteenth embodiment includes methods according to the eleventh and/or twelfth embodiments wherein an herbicidally effective amount of the mixture is applied either pre- or post-emergently to at least one of the following: a crop, a field, a ROW, or a rice paddy.

A fourteenth embodiment includes methods according to the tenth through the thirteenth embodiments wherein the undesirable vegetation may be controlled in: glyphosate-5-enolpyruvylshikimate-3-phosphate (EPSP) synthase inhibitor-, glufosinate-, glutamine synthetase inhibitor-, dicamba-, phenoxy auxin-, pyridyloxy auxin-, synthetic auxin-, auxin transport inhibitor-, aryloxyphenoxypropionate-, cyclohexanedione-, phenylpyrazoline-, acetyl CoA carboxylase (ACCase) inhibitor-, imidazolinone-, sulfonylurea-, pyrimidinylthiobenzoate-, triazolopyrimidine-, sulfonylaminocarbonyltriazolinone-, acetolactate synthase (ALS) or acetohydroxy acid synthase (AHAS) inhibitor-, 4-hydroxyphenyl-pyruvate dioxygenase (HPPD) inhibitor-, phytoene desaturase inhibitor-, carotenoid biosynthesis inhibitor-, protoporphyrinogen oxidase (PPO) inhibitor-, cellulose biosynthesis inhibitor-, mitosis inhibitor-, microtubule inhibitor-, very long chain fatty acid inhibitor-, fatty acid and lipid biosynthesis inhibitor-, photosystem I inhibitor-, photosystem II inhibitor-, protoporphyrinogen oxidase (PPO) inhibitor-, triazine-, or bromoxynil-tolerant crops.

A fifteenth embodiment includes a at least one method according to the eleventh through the fourteenth embodiments wherein a plant that is resistant or tolerant to at least one herbicide is treated, and where the resistant tolerant crop possesses multiple or stacked traits conferring tolerance to multiple herbicides or inhibitors of multiple modes of action, in some embodiments the treated plant that expresses resistance or tolerance to an herbicide is a itself undesirable vegetation.

A sixteenth embodiment includes methods according to the fifteenth embodiment, wherein the resistant or tolerant weed is a biotype with resistance or tolerance to multiple herbicides, multiple chemical classes, inhibitors of multiple herbicide modes-of-action, or via multiple resistance mechanisms.

A seventeenth embodiment includes at least one of the methods according to the fifteenth or sixteenth embodiments, wherein the resistant or tolerant undesirable plant is a biotype resistant or tolerant to at least one or more modes of action consisting of: acetolactate synthase (ALS) inhibitors or acetohydroxy acid synthase (AHAS) inhibitors, photosystem II inhibitors, acetyl CoA carboxylase (ACCase) inhibitors, synthetic auxins, auxin transport inhibitors, photosystem I inhibitors, 5-enolpyruvylshikimate-3-phosphate (EPSP) synthase inhibitors, microtubule assembly inhibitors, fatty acid and lipid synthesis inhibitors, protoporphyrinogen oxidase (PPO) inhibitors, carotenoid biosynthesis inhibitors, very long chain fatty acid (VLCFA) inhibitors, phytoene desaturase (PDS) inhibitors, glutamine synthetase inhibitors, 4-hydroxyphenyl-pyruvate-dioxygenase (HPPD) inhibitors, mitosis inhibitors, cellulose biosynthesis inhibitors, herbicides with multiple modes-of-action, quinclorac, arylaminopropionic acids, difenzoquat, endothall, or organoarsenicals.

An eighteenth embodiment includes methods of controlling undesirable vegetation comprising the step of applying an herbicidally effective amount of at least one mixture according to the fourth embodiment wherein the amount of the mixture is applied at a rate, expressed in gai/ha or gae/ha of imazethapyr selected from the group of rates and ranges of rates consisting of, about: 1.2, 8.75, 17.5, 7.0, 35, 70, 140 and 200.

A nineteenth embodiment includes methods according to the fourth and eighteenth embodiments wherein the controlled plant is at least one plant selected from the group consisting of: LEFCH, CYPES, DIGSA, ECHCG, ECHOR and AVEFA, still other embodiments include controlling plants from the genera consisting of: *Leptochloa, Cyperus, Digitaria, Echinochloa*, and *Avena*.

A twentieth embodiment includes methods of controlling undesirable vegetation comprising the step of applying an herbicidally effective amount of at least one a mixture according to the fifth embodiment wherein the amount of the mixture is applied at a rate, expressed in gai/ha or gae/ha of imazamox selected from the group of rates and ranges of rates consisting of, about: 1.0, 5.6, 11.2, 22.4, 44.8 and 100.

A twenty-first embodiment includes methods according to the fifth and twentieth embodiments wherein the controlled plant is at least one plant selected from the group consisting of: LEFCH, CYPES, CYPIR, ECHOR, and ECHCG, still other embodiments include controlling plants from the genera consisting of: *Leptochloa, Cyperus*, and *Echinochloa*.

A twenty-second embodiment includes methods of controlling undesirable vegetation comprising the step of applying an herbicidally effective amount of at least one a mixture according to the sixth embodiment wherein the amount of the mixture is applied at a rate, expressed in gai/ha or gae/ha of imazapic selected from the group of rates and ranges of rates consisting of, about: 1, 2, 4.3, 7.0, 8.75, 17.5, 35, 70, 140, and 200.

A twenty-third embodiment includes methods according to the sixth and twenty-second embodiments wherein the controlled plant is at least one plant selected from the group consisting of: ECHCO, LEFCH, CYPIR, IPOHE, ECHOR, ECHCG, ALOMY, AVEFA, CENMA, and SONAR, still other embodiments include controlling plants from the genera consisting of: *Brachiaria, Cyperus, Leptochloa, Echinochloa, Ipomoea, Alopecurus, Sonchus, Centaurea* and *Avena*.

A twenty-fourth embodiment includes methods of controlling undesirable vegetation comprising the step of applying an herbicidally effective amount of at least one a mixture according to the seventh embodiment wherein the amount of the mixture is applied at a rate, expressed in gai/ha or gae/ha of imazapyr selected from the group of rates and ranges of rates consisting of, about: 1, 2, 4.8, 8.75, 70, 140, and 280.

A twenty-fifth embodiment includes methods according to the seventh and twenty-fourth embodiments wherein the controlled plant is at least one plant selected from the group consisting of: IPOHE, ECHOR, and CYPRO, still other embodiments include controlling plants from the genera consisting of: *Ipomoea, Echinochloa*, and *Cyperus*.

A twenty-sixth embodiment includes methods of controlling undesirable vegetation comprising the step of applying an herbicidally effective amount of at least one a mixture according to the eighth embodiment wherein the amount of the mixture is applied at a rate, expressed in gai/ha or gae/ha of imazamethabenz-methyl selected from the group of rates and ranges of rates consisting of, about: 1, 2, 43.75, 87.5, 175, 200, 350, 400 and the range 1:400.

A twenty-seventh embodiment includes methods according to the eighth and twenty-sixth embodiments wherein the controlled plant is at least one plant selected from the group consisting of: CYPIR, CHEAL, CIRAR, PAPRH, SASKR, and VERPE, still other embodiments include controlling plants from the genera consisting of: *Cyperus, Chenopodium, Cirsium, Papaver, Veronica,* and *Salsola.*

A twenty-eighth embodiment includes methods of controlling undesirable vegetation comprising the step of applying an herbicidally effective amount of at least one a mixture according to the ninth embodiment wherein the amount of the mixture is applied at a rate, expressed in gai/ha or gae/ha of imazaquin selected from the group of rates and ranges of rates consisting of, about: 1, 2, 9, 18, 36, 75, and 100, and the range 1:100.

A twenty-ninth embodiment includes methods according to the ninth and twenty-eighth embodiments wherein the controlled plant is at least one plant selected from the group consisting of: IPOHE and CLRAR, still other embodiments include controlling plants from the genus *Ipomoea* and *Cirsium*.

DETAILED DESCRIPTION

Definitions

As used herein, the compound of formula (I) has the following structure:

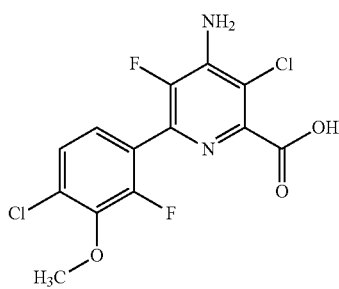

(I)

The compound of formula (I) can be identified by the name 4-amino-3-chloro-6-(4-chloro-2-fluoro-3-methoxyphenyl)-5-fluoropyridine-2-carboxylic acid and has been described in U.S. Pat. No. 7,314,849 (B2), which is incorporated herein by reference in its entirety. Exemplary uses of the compound of the formula (I) include controlling undesirable vegetation, including but not limited to grass, broadleaf and sedge weeds, in multiple non-crop and cropping situations.

Imidazolinones are a class of widely used herbicides known in the art. Without being limited to any theory, these herbicides kill plants by inhibiting acetohydroxyacid synthase, the first common enzyme in the biosynthesis of the branched chain amino acids. Exemplary uses of imidazolinones include their use as herbicides in legumes, cereals and resistant crops.

Exemplary imidazolinones include, but are not limited to, imazethapyr, imazamox, imazapic, imazapyr, imazamethabenz and imazaquin.

As used herein, imazethapyr is (±)-2-[4,5-dihydro-4-methyl-4-(1-methylethyl)-5-oxo-1H-imidazol-2-yl]-5-ethyl-3-pyridinecarboxylic acid and possesses the following structure:

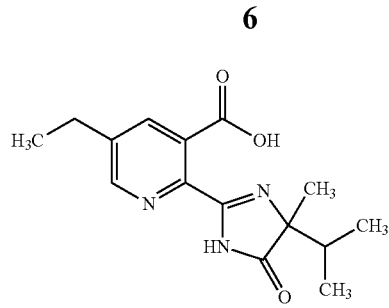

Its herbicidal activity is exemplified in Tomlin, C., ed. A World Compendium The Pesticide Manual. 15$^{th}$ ed. Alton: BCPC Publications, 2009 (hereafter "*The Pesticide Manual*, Fifteenth Edition, 2009."). Exemplary uses of imazethapyr include its use for either pre- or post-emergence control of annual and perennial grass and broadleaf weeds in crops.

As used herein, imazethapyr ammonium is ammonium (±)-2-[4,5-dihydro-4-methyl-4-(1-methylethyl)-5-oxo-1H-imidazol-2-yl]-5-ethyl-3-pyridinecarboxylate and possesses the following structure:

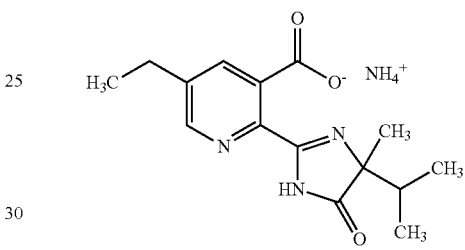

As used herein, imazamox is (±)-2-[4,5-dihydro-4-methyl-4-(1-methylethyl)-5-oxo-1H-imidazol-2-yl]-5-(methoxymethyl)-3-pyridinecarboxylic acid and possesses the following structure:

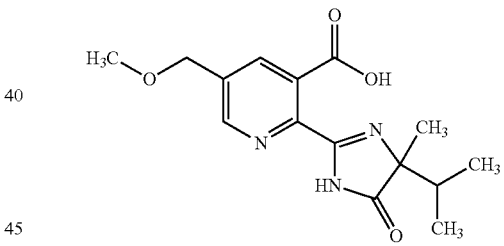

Its herbicidal activity is exemplified in *The Pesticide Manual*, Fifteenth Edition, 2009. Exemplary uses of imazamox include its use for either pre- or post-emergence control of broadleaf and grass weeds, e.g., in rice, maize, rape, alfalfa, peas and beans.

As used herein, imazamox ammonium is ammonium (±)-2-[4,5-dihydro-4-methyl-4-(1-methylethyl)-5-oxo-1H-imidazol-2-yl]-5-(methoxymethyl)-3-pyridinecarboxylate and possesses the following structure:

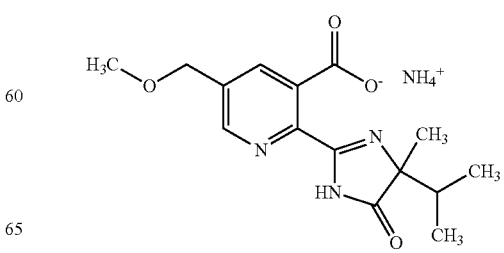

As used herein, imazapic is (±)-2-[4,5-dihydro-4-methyl-4-(1-methylethyl)-5-oxo-1H-imidazol-2-yl]-5-methyl-3-pyridinecarboxylic acid and possesses the following structure:

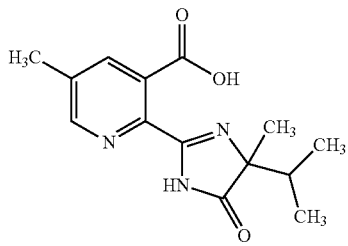 [SMILES: Cc1cnc(C2=NC(C)(C(C)C)C(=O)N2)c(C(=O)O)c1]

Its herbicidal activity is exemplified in *The Pesticide Manual*, Fifteenth Edition, 2009. Exemplary uses of imazapic include its use for either pre- or post-emergence control of weeds in pasture, rangeland and non-cropland areas.

As used herein, imazapic ammonium is ammonium (±)-2-[4,5-dihydro-4-methyl-4-(1-methylethyl)-5-oxo-1H-imidazol-2-yl]-5-methyl-3-pyridinecarboxylic acid and possesses the following structure:

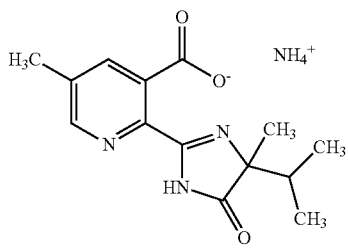 [SMILES: Cc1cnc(C2=NC(C)(C(C)C)C(=O)N2)c(C(=O)[O-])c1 ; [NH4+]]

Its herbicidal activity is exemplified in *The Pesticide Manual*, Fifteenth Edition, 2009. Exemplary uses of imazapic include its use for either pre- or post-emergence control of weeds in pasture, rangeland and non-cropland areas.

As used herein, imazapyr is the common name for (±)-2-[4,5-dihydro-4-methyl-4-(1-methylethyl)-5-oxo-1H-imidazol-2-yl]-3-pyridinecarboxylic acid and possesses the following structure:

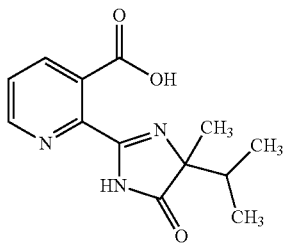 [SMILES: CC(C)C1(C)N=C(c2ncccc2C(=O)O)NC1=O]

Its herbicidal activity is exemplified in *The Pesticide Manual*, Fifteenth Edition, 2009. Exemplary uses of imazapyr include its use for either pre- or post-emergence control of annual and perennial grasses, broadleaf weeds, brush and trees.

As used herein, imazapyr isopropylammonium is the common name for 2-[4,5-dihydro-4-methyl-4-(1-methylethyl)-5-oxo-1H-imidazol-2-yl]-3-pyridinecarboxylic acid compound with 2-propanamine and possesses the following structure:

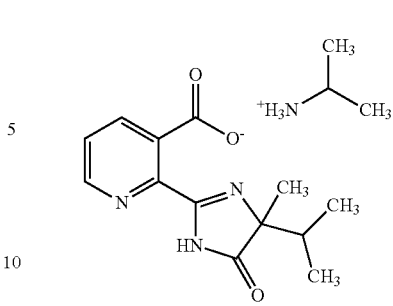

As used herein, imazamethabenz is the common name for 2-[4,5-dihydro-4-methyl-4-(1-methylethyl)-5-oxo-1H-imidazol-2-yl]-4-methylbenzoic acid or 2-[4,5-dihydro-4-methyl-4-(1-methylethyl)-5-oxo-1H-imidazol-2-yl]-5-methylbenzoic acid or mixtures thereof, possessing the following structures i and ii respectively:

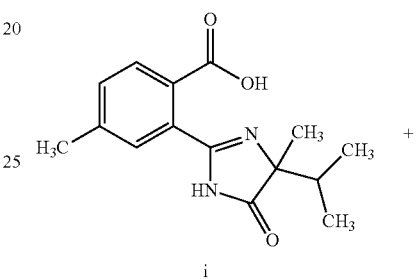

i

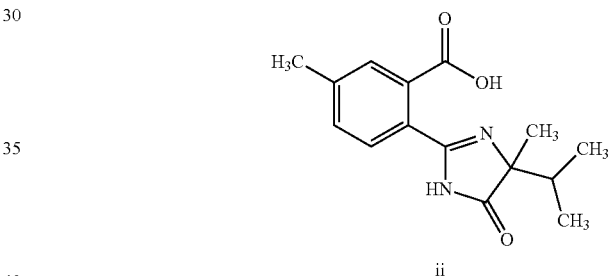

ii

Its herbicidal activity is exemplified in *The Pesticide Manual*, Fifteenth Edition, 2009. Exemplary uses of imazamethabenz include its use for post-emergence control of *Avena* species, *Alopecurus myosuroides*, *Apera spica-venti* and dicotyledonous weeds in wheat, barley, rye and sunflowers.

As used herein, imazamethabenz-methyl is the common name for methyl 2-[4,5-dihydro-4-methyl-4-(1-methylethyl)-5-oxo-1H-imidazol-2-yl]-4-methylbenzoic acid or methyl 2-[4,5-dihydro-4-methyl-4-(1-methylethyl)-5-oxo-1H-imidazol-2-yl]-5-methylbenzoic acid or mixtures thereof, possessing the following structures i and ii respectively:

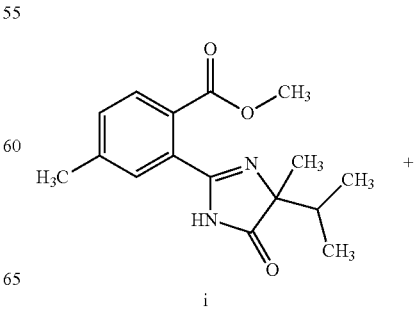

i

-continued

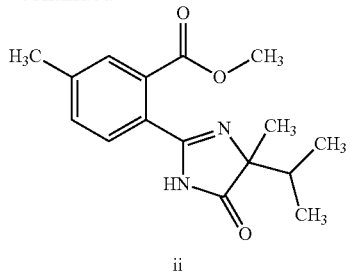

ii

Its herbicidal activity is exemplified in *The Pesticide Manual*, Fifteenth Edition, 2009. Exemplary uses of imazamethabenz include its use for post-emergence control of *Avena* species, *Alopecurus myosuroides*, *Apera spica-venti* and dicotyledonous weeds in wheat, barley, rye and sunflowers.

As used herein, imazaquin is the common name for (±)-2-[4,5-dihydro-4-methyl-4-(1-methylethyl)-5-oxo-1H-imidazol-2-yl]-3-quinolinecarboxylic acid and possesses the following structure:

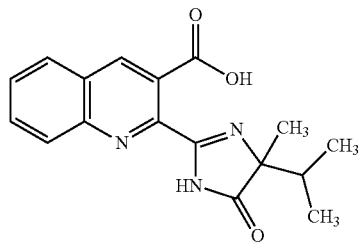 [SMILES: CC(C)C1(C)N=C(c2nc3ccccc3cc2C(=O)O)NC1=O]

Its herbicidal activity is exemplified in *The Pesticide Manual*, Fifteenth Edition, 2009. Exemplary uses of imazaquin include its use for pre-planting, pre-emergence or early post-emergence control of broadleaf weeds, e.g., in soybeans. As used herein, imazaquin isopropylammonium is the common name for (±)-2-[4,5-dihydro-4-methyl-4-(1-methylethyl)-5-oxo-1H-imidazol-2-yl]-3-quinolinecarboxylic acid with 2-propanamine and possesses the following structure:

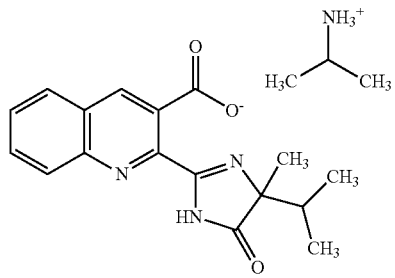

Its herbicidal activity is exemplified in *The Pesticide Manual*, Fifteenth Edition, 2009. Exemplary uses of imazaquin include its use for pre-planting, pre-emergence or early post-emergence control of broadleaf weeds, e.g., in soybeans.

As used herein, herbicide means a compound, e.g., an active ingredient that kills, controls, or otherwise adversely modifies the growth of plants.

As used herein, an herbicidally effective or vegetation controlling amount is an amount of active ingredient which causes an adversely modifying effect to the vegetation e.g., causing deviations from natural development, killing, effecting regulation, causing desiccation, causing retardation, and the like.

As used herein, controlling undesirable vegetation means preventing, reducing, killing, or otherwise adversely modifying the development of plants and vegetation. Described herein are methods of controlling undesirable vegetation through the application of certain herbicide combinations or compositions. Methods of application include, but are not limited to applications to the vegetation or locus thereof, e.g., application to the area adjacent to the vegetation, as well as preemergence, postemergence, foliar (broadcast, directed, banded, spot, mechanical, over-the-top, or rescue), and in-water applications (emerged and submerged vegetation, broadcast, spot, mechanical, water-injected, granular broadcast, granular spot, shaker bottle, or stream spray) via hand, backpack, machine, tractor, or aerial (airplane and helicopter) application methods.

As used herein, plants and vegetation include, but are not limited to, germinant seeds, emerging seedlings, plants emerging from vegetative propagules, immature vegetation, and established vegetation.

As used herein, agriculturally acceptable salts and esters refer to salts and esters that exhibit herbicidal activity, or that are or can be converted in plants, water, or soil to the referenced herbicide. Exemplary agriculturally acceptable esters are those that are or can be hydrolyzed, oxidized, metabolized, or otherwise converted, e.g., in plants, water, or soil, to the corresponding carboxylic acid which, depending on the pH, may be in the dissociated or undissociated form.

Exemplary salts include those derived from alkali or alkaline earth metals and those derived from ammonia and amines. Exemplary cations include sodium, potassium, magnesium, and ammonium cations of the formula:

$$R^1R^2R^3R^4N^+$$

wherein $R^1$, $R^2$, $R^3$ and $R^4$ each, independently represents hydrogen or $C_1$-$C_{12}$ alkyl, $C_3$-$C_{12}$ alkenyl or $C_3$-$C_{12}$ alkynyl, each of which is optionally substituted by one or more hydroxy, $C_1$-$C_4$ alkoxy, $C_1$-$C_4$ alkylthio or phenyl groups, provided that $R^1$, $R^2$, $R^3$ and $R^4$ are sterically compatible. Additionally, any two of $R^1$, $R^2$, $R^3$ and $R^4$ together may represent an aliphatic difunctional moiety containing one to twelve carbon atoms and up to two oxygen or sulfur atoms. Salts can be prepared by treatment with a metal hydroxide, such as sodium hydroxide, with an amine, such as ammonia, trimethylamine, diethanolamine, 2-methylthiopropylamine, bisallylamine, 2-butoxyethylamine, morpholine, cyclododecylamine, or benzylamine or with a tetraalkylammonium hydroxide, such as tetramethylammonium hydroxide or choline hydroxide.

Exemplary esters include those derived from $C_1$-$C_{12}$ alkyl, $C_3$-$C_{12}$ alkenyl, $C_3$-$C_{12}$ alkynyl or $C_7$-$C_{10}$ aryl-substituted alkyl alcohols, such as methyl alcohol, isopropyl alcohol, 1-butanol, 2-ethylhexanol, butoxyethanol, methoxypropanol, allyl alcohol, propargyl alcohol, cyclohexanol or unsubstituted or substituted benzyl alcohols. Benzyl alcohols may be substituted with from 1-3 substituents independently selected from halogen, $C_1$-$C_4$ alkyl or $C_1$-$C_4$ alkoxy. Esters can be prepared by coupling of the acids with the alcohol using any number of suitable activating agents such as those used for peptide couplings such as dicyclohexylcarbodiimide (DCC) or carbonyl diimidazole (CDI); by reacting the acids with alkylating agents such as alkylhalides or alkylsulfonates in the presence of a base such as triethylamine or lithium carbonate; by reacting the corresponding acid chloride of an acid with an appropriate alcohol; by reacting the corresponding acid with an appropriate alcohol in the presence of an acid catalyst or by transesterification.

Compositions and Methods

Provided herein are herbicidal compositions comprising an herbicidally effective amount of (a) a compound of the formula (I)

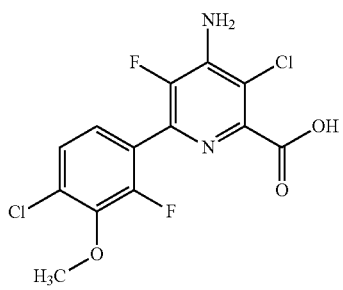

or an agriculturally acceptable salt or ester thereof, and (b) an imidazolinone.

Provided herein are also methods of controlling undesirable vegetation comprising contacting the vegetation or the locus thereof, i.e., area adjacent to the vegetation, with or applying to the soil or water to prevent the emergence or growth of vegetation an herbicidally effective amount of the compound of formula (I) or agriculturally acceptable salt or ester thereof and (b) an imidazolinone. In certain embodiments, the methods employ the compositions described herein.

Furthermore, in some embodiments, the combination of compound (I) or agriculturally acceptable salt or ester thereof and imidazolinones exhibits synergism, e.g., the herbicidal active ingredients are more effective in combination than when applied individually. Synergism has been defined as "an interaction of two or more factors such that the effect when combined is greater than the predicted effect based on the response of each factor applied separately." Senseman, S., ed. Herbicide Handbook. $9^{th}$ ed. Lawrence: Weed Science Society of America, 2007. In certain embodiments, the compositions exhibit synergy as determined by the Colby's equation. Colby, S. R. 1967. Calculation of the synergistic and antagonistic response of herbicide combinations. Weeds 15:20-22.

In certain embodiments of the compositions and methods described herein, the compound of formula (I), i.e., the carboxylic acid, is employed. In certain embodiments, a carboxylate salt of the compound of formula (I) is employed. In certain embodiments, an aralkyl or alkyl ester is employed. In certain embodiments, a benzyl, substituted benzyl, or $C_{1-4}$ alkyl, e.g., n-butyl ester is employed. In certain embodiments, the benzyl ester is employed.

In some embodiments, the compound of formula (I) or salt or ester thereof and imidazolinone are formulated in one composition, tank mixed, applied simultaneously, or applied sequentially.

Herbicidal activity is exhibited by the compounds when they are applied directly to the plant or to the locus of the plant at any stage of growth. The effect observed depends upon the plant species to be controlled, the stage of growth of the plant, the application parameters of dilution and spray drop size, the particle size of solid components, the environmental conditions at the time of use, the specific compound employed, the specific adjuvants and carriers employed, the soil type, and the like, as well as the amount of chemical applied. These and other factors can be adjusted to promote non-selective or selective herbicidal action. In some embodiments, the compositions described herein are applied as a post-emergence application, pre-emergence application, or in-water application to flooded paddy rice or water bodies (e.g., ponds, lakes and streams), to relatively immature undesirable vegetation to achieve the maximum control of weeds.

In some embodiments, the compositions and methods provided herein are utilized to control weeds in crops, including but not limited to direct-seeded, water-seeded and transplanted rice, cereals, wheat, barley, oats, rye, sorghum, corn/maize, sugarcane, sunflower, oilseed rape, canola, sugar beet, soybean, cotton, pineapple, pastures, grasslands, rangelands, fallowland, turf, tree and vine orchards, aquatics, plantation crops, vegetables, industrial vegetation management (IVM) and rights of way (ROW).

In certain embodiments, the compositions and methods provided herein are utilized to control weeds in rice. In certain embodiments, the rice is direct seeded, water seeded, or transplanted rice.

The compositions and methods described herein may be used to control undesirable vegetation in glyphosate-tolerant-, 5-enolpyruvylshikimate-3-phosphate (EPSP) synthase inhibitor-tolerant-, glufosinate-tolerant-, glutamine synthetase inhibitor-tolerant-, dicamba-tolerant-, phenoxy auxin-tolerant-, pyridyloxy auxin-tolerant-, auxin-tolerant-, auxin transport inhibitor-tolerant-, aryloxyphenoxypropionate-tolerant-, cyclohexanedione-tolerant-, phenylpyrazoline-tolerant-, acetyl CoA carboxylase (ACCase) inhibitor-tolerant-, imidazolinone-tolerant-, sulfonylurea-tolerant-, pyrimidinylthiobenzoate-tolerant-, triazolopyrimidine-tolerant-, sulfonylaminocarbonyltriazolinone-tolerant-, acetolactate synthase (ALS) or acetohydroxy acid synthase (AHAS) inhibitor-tolerant-, 4-hydroxyphenyl-pyruvate dioxygenase (HPPD) inhibitor-tolerant-, phytoene desaturase inhibitor-tolerant-, carotenoid biosynthesis inhibitor-tolerant-, protoporphyrinogen oxidase (PPO) inhibitor-tolerant-, cellulose biosynthesis inhibitor-tolerant-, mitosis inhibitor-tolerant-, microtubule inhibitor-tolerant-, very long chain fatty acid inhibitor-tolerant-, fatty acid and lipid biosynthesis inhibitor-tolerant-, photosystem I inhibitor-tolerant-, photosystem II inhibitor-tolerant-, triazine-tolerant- and bromoxynil-tolerant-crops (such as, but not limited to, soybean, cotton, canola/oilseed rape, rice, cereals, corn, sorghum, sunflower, sugar beet, sugarcane, turf, etc.), for example, in conjunction with glyphosate, EPSP synthase inhibitors, glufosinate, glutamine synthase inhibitors, dicamba, phenoxy auxins, pyridyloxy auxins, synthetic auxins, auxin transport inhibitors, aryloxyphenoxypropionates, cyclohexanediones, phenylpyrazolines, ACCase inhibitors, imidazolinones, sulfonylureas, pyrimidinylthiobenzoates, triazolopyrimidines, sulfonylaminocarbonyltriazolinones, ALS or AHAS inhibitors, HPPD inhibitors, phytoene desaturase inhibitors, carotenoid biosynthesis inhibitors, PPO inhibitors, cellulose biosynthesis inhibitors, mitosis inhibitors, microtubule inhibitors, very long chain fatty acid inhibitors, fatty acid and lipid biosynthesis inhibitors, photosystem I inhibitors, photosystem II inhibitors, triazines, and bromoxynil The compositions and methods may be used in controlling undesirable vegetation in crops possessing multiple or stacked traits conferring tolerance to multiple chemistries and/or inhibitors of multiple modes of action. In some embodiments, the compound of formula (I) or salt or ester thereof and complementary herbicide or salt or ester thereof are used in combination with herbicides that are selective for the crop being treated and which complement the spectrum of weeds controlled by these compounds at the application rate employed. In some embodiments, the compositions described herein and other complementary herbicides are applied at the same time, either as a combination formulation, as a tank mix or sequentially.

The compositions and methods may be used in controlling undesirable vegetation in crops possessing agronomic stress tolerance (including but not limited to drought, cold, heat, salt, water, nutrient, fertility, pH), pest tolerance (including but not limited to insects, fungi and pathogens) and crop improvement traits (including but not limited to yield; protein, carbohydrate, or oil content; protein, carbohydrate, or oil composition; plant stature and plant architecture).

The compositions and methods provided herein are utilized to control undesirable vegetation. Undesirable vegetation includes, but is not limited to, undesirable vegetation that occurs in rice, cereals, wheat, barley, oats, rye, pastures, grasslands, rangelands, fallowland, row crops (e.g., corn/maize, sugarcane, sunflower, oilseed rape, canola, sugar beet, soybean, cotton), turf, trees and vine orchards, plantation crops, vegetables, ornamental species, aquatic or non-crop settings, (e.g., rights-of-way, industrial vegetation management).

In some embodiments, the methods provided herein are utilized to control undesirable vegetation in rice. In certain embodiments, the undesirable vegetation is *Brachiaria platyphylla* (Groseb.) Nash or *Urochloa platyphylla* (Nash) R. D. Webster (broadleaf signalgrass, BRAPP), *Digitaria sanguinalis* (L.) Scop. (large crabgrass, DIGSA), *Echinochloa* species (ECHSS), *Echinochloa crus-galli* (L.) P. Beauv. (barnyardgrass, ECHCG), *Echinochloa crus-pavonis* (Kunth) Schuh. (gulf cockspur, ECHCV), *Echinochloa colonum* (L.) LINK (junglerice, ECHCO), *Echinochloa oryzoides* (Ard.) Fritsch (early watergrass, ECHOR), *Echinochloa oryzicola* (Vasinger) Vasinger (late watergrass, ECHPH), *Echinochloa phyllopogon* (Stapf) Koso-Pol. (rice barnyardgrass, ECHPH), *Echinochloa polystachya* (Kunth) Hitchc. (creeping river grass, ECHPO), *Ischaemum rugosum* Salisb. (saramollagrass, ISCRU), *Leptochloa chinensis* (L.) Nees (Chinese sprangletop, LEFCH), *Leptochloa fascicularis* (Lam.) Gray (bearded sprangletop, LEFFA), *Leptochloa panicoides* (Presl.) Hitchc. (Amazon sprangletop, LEFPA), *Oryza* species (red and weedy rice, ORYSS), *Panicum dichotomiflorum* (L.) Michx. (fall panicum, PANDI), *Paspalum dilatatum* Poir. (dallisgrass, PASDI), *Rottboellia cochinchinensis* (Lour.) W. D. Clayton (itchgrass, ROOEX), *Cyperus* species (CYPSS), *Cyperus difformis* L. (smallflower flatsedge, CYPDI), *Cyperus dubius* Rottb. (MAPDU), *Cyperus esculentus* L. (yellow nutsedge, CYPES), *Cyperus iria* L. (rice flatsedge, CYPIR), *Cyperus rotundus* L. (purple nutsedge, CYPRO), *Cyperus serotinus* Rottb./C. B. Clarke (tidalmarsh flatsedge, CYPSE), *Eleocharis* species (ELOSS), *Fimbristylis miliacea* (L.) Vahl (globe fringerush, FIMMI), *Schoenoplectus* species (SCPSS), *Schoenoplectus juncoides* Roxb. (Japanese bulrush, SCPJU), *Bolboschoenus maritimus* (L.) Palla or *Schoenoplectus maritimus* L. Lye (sea clubrush, SCPMA), *Schoenoplectus mucronatus* L. (ricefield bulrush, SCPMU), *Aeschynomene* species, (jointvetch, AESSS), *Alternanthera philoxeroides* (Mart.) Griseb. (alligatorweed, ALRPH), *Alisma plantago-aquatica* L. (common waterplantain, ALSPA), *Amaranthus* species, (pigweeds and amaranths, AMASS), *Ammannia coccinea* Rottb. (redstem, AMMCO), *Commelina benghalensis* L. (Benghal dayflower, COMBE), *Eclipta alba* (L.) Hassk. (American false daisy, ECLAL), *Heteranthera limosa* (SW.) Willd./Vahl (ducksalad, HETLI), *Heteranthera reniformis* R. & P. (roundleaf mudplantain, HETRE), *Ipomoea* species (morningglories, IPOSS), *Ipomoea hederacea* (L.) Jacq. (ivyleaf morningglory, IPOHE), *Lindernia dubia* (L.) Pennell (low false pimpernel, LIDDU), *Ludwigia* species (LUDSS), *Ludwigia linifolia* Poir. (southeastern primrose-willow, LUDLI), *Ludwigia octovalvis* (Jacq.) Raven (longfruited primrose-willow, LUDOC), *Monochoria korsakowii* Regel & Maack (monochoria, MOOKA), *Monochoria vaginalis* (Burm. F.) C. Presl ex Kuhth, (monochoria, MOOVA), *Murdannia nudiflora* (L.) Brenan (doveweed, MUDNU), *Polygonum pensylvanicum* L., (Pennsylvania smartweed, POLPY), *Polygonum persicaria* L. (ladysthumb, POLPE), *Polygonum hydropiperoides* Michx. (POLHP, mild smartweed), *Rotala indica* (Willd.) Koehne (Indian toothcup, ROTIN), *Sagittaria* species, (arrowhead, SAGSS), *Sesbania exaltata* (Raf.) Cory/Rydb. Ex Hill (hemp sesbania, SEBEX), or *Sphenoclea zeylanica* Gaertn. (gooseweed, SPDZE).

In some embodiments, the methods provided herein are utilized to control undesirable vegetation in cereals. In certain embodiments, the undesirable vegetation is *Alopecurus myosuroides* Huds. (blackgrass, ALOMY), *Apera spica-venti* (L.) Beauv. (windgrass, APESV), *Avena fatua* L. (wild oat, AVEFA), *Bromus tectorum* L. (downy brome, BROTE), *Lolium multflorum* Lam. (Italian ryegrass, LOLMU), *Phalaris minor* Retz. (littleseed canarygrass, PHAMI), *Poa annua* L. (annual bluegrass, POANN), *Setaria pumila* (Poir.) Roemer & J. A. Schultes (yellow foxtail, SETLU), *Setaria viridis* (L.) Beauv. (green foxtail, SETVI), *Amaranthus retroflexus* L. (redroot pigweed, AMARE), *Brassica* species (BRSSS), *Chenopodium album* L. (common lambsquarters, CHEAL), *Cirsium arvense* (L.) Scop. (Canada thistle, CIRAR), *Galium aparine* L. (catchweed bedstraw, GALAP), *Kochia scoparia* (L.) Schrad. (kochia, KCHSC), *Lamium purpureum* L. (purple deadnettle, LAMPU), *Matricaria recutita* L. (wild chamomile, MATCH), *Matricaria matricarioides* (Less.) Porter (pineappleweed, MATMT), *Papaver rhoeas* L. (common poppy, PAPRH), *Polygonum convolvulus* L. (wild buckwheat, POLCO), *Salsola tragus* L. (Russian thistle, SASKR), *Sinapis* species (SINSS), *Sinapis arvensis* L. (wild mustard, SINAR), *Stellaria media* (L.) Vill. (common chickweed, STEME), *Veronica persica* Poir. (Persian speedwell, VERPE), *Viola arvensis* Murr. (field violet, VIOAR), or *Viola tricolor* L. (wild violet, VIOTR).

In some embodiments, the methods provided herein are utilized to control undesirable vegetation in range and pasture, fallowland, IVM and ROW. In certain embodiments, the undesirable vegetation is *Ambrosia artemisiifolia* L. (common ragweed, AMBEL), *Cassia obtusifolia* (sickle pod, CASOB), *Centaurea maculosa* auct. non Lam. (spotted knapweed, CENMA), *Cirsium arvense* (L.) Scop. (Canada thistle, CIRAR), *Convolvulus arvensis* L. (field bindweed, CONAR), *Daucus carota* L. (wild carrot, DAUCA), *Euphorbia esula* L. (leafy spurge, EPHES), *Lactuca serriola* L./Torn. (prickly lettuce, LACSE), *Plantago lanceolata* L. (buckhorn plantain, PLALA), *Rumex obtusifolius* L. (broadleaf dock, RUMOB), *Sida spinosa* L. (prickly sida, SIDSP), *Sinapis arvensis* L. (wild mustard, SINAR), *Sonchus arvensis* L. (perennial sowthistle, SONAR), *Solidago* species (goldenrod, SOOSS), *Taraxacum officinale* G. H. Weber ex Wiggers (dandelion, TAROF), *Trifolium repens* L. (white clover, TRFRE), or *Urtica dioica* L. (common nettle, URTDI).

In some embodiments, the methods provided herein are utilized to control undesirable vegetation found in row crops, tree and vine crops, and perennial crops. In certain embodiments, the undesirable vegetation is *Alopecurus myosuroides* Huds. (blackgrass, ALOMY), *Avena fatua* L. (wild oat, AVEFA), *Brachiaria decumbens* Stapf. or *Urochloa decumbens* (Stapf) R. D. Webster (Surinam grass, BRADC), *Brachiaria brizantha* (Hochst. ex A. Rich.) Stapf. or *Urochloa brizantha* (Hochst. ex A. Rich.) R. D. (beard grass, BRABR),

*Brachiaria platyphylla* (Groseb.) Nash or *Urochloa platyphylla* (Nash) R. D. Webster (broadleaf signalgrass, BRAPP), *Brachiaria plantaginea* (Link) Hitchc. or *Urochloa plantaginea* (Link) R. D. Webster (alexandergrass, BRAPL), *Cenchrus echinatus* L. (southern sandbar, CENEC), *Digitaria horizontalis* Willd. (Jamaican crabgrass, DIGHO), *Digitaria insularis* (L.) Mez ex Ekman (sourgrass, TRCIN), *Digitaria sanguinalis* (L.) Scop. (large crabgrass, DIGSA), *Echinochloa crus-galli* (L.) P. Beauv. (barnyardgrass, ECHCG), *Echinochloa colonum* (L.) Link (junglerice, ECHCO), *Eleusine indica* (L.) Gaertn. (goosegrass, ELEIN), *Lolium multiflorum* Lam. (Italian ryegrass, LOLMU), *Panicum dichotomiflorum* Michx. (fall *panicum*, PANDI), *Panicum miliaceum* L. (wild-proso millet, PANMI), *Setaria faberi* Herrm. (giant foxtail, SETFA), *Setaria viridis* (L.) Beauv. (green foxtail, SETVI), *Sorghum halepense* (L.) Pers. (Johnsongrass, SORHA), *Sorghum bicolor* (L.) *Moench* ssp. *Arundinaceum* (shattercane, SORVU), *Cyperus esculentus* L. (yellow nutsedge, CYPES), *Cyperus rotundus* L. (purple nutsedge, CYPRO), *Abutilon theophrasti* Medik. (velvetleaf, ABUTH), *Amaranthus* species (pigweeds and amaranths, AMASS), *Ambrosia artemisiifolia* L. (common ragweed, AMBEL), *Ambrosia psilostachya* DC. (western ragweed, AMBPS), *Ambrosia trifida* L. (giant ragweed, AMBTR), *Anoda cristata* (L.) Schlecht. (spurred anoda, ANVCR), *Asclepias syriaca* L. (common milkweed, ASCSY), *Bidens pilosa* L. (hairy beggarticks, BIDPI), *Borreria* species (BOISS), *Borreria alata* (Aubl.) DC. or *Spermacoce alata* Aubl. (broadleaf buttonweed, BOILF), *Spermacose latifolia* (broadleaved button weed, BOILF), *Chenopodium album* L. (common lambsquarters, CHEAL), *Cirsium arvense* (L.) Scop. (Canada thistle, CIRAR), *Commelina benghalensis* L. (tropical spiderwort, COMBE), *Datura stramonium* L. (jimsonweed, DATST), *Daucus carota* L. (wild carrot, DAUCA), *Euphorbia heterophylla* L. (wild poinsettia, EPHHL), *Euphorbia hirta* L. or *Chamaesyce hirta* (L.) Millsp. (garden spurge, EPHHI), *Euphorbia dentata* Michx. (toothed spurge, EPHDE), *Erigeron bonariensis* L. or Conyza bonariensis (L.) Cronq. (hairy fleabane, ERIBO), *Erigeron canadensis* L. (Canadian fleabane, ERICA), *Conyza sumatrensis* (Retz.) E. H. Walker (tall fleabane, ERIFL), *Helianthus annuus* L. (common sunflower, HELAN), *Jacquemontia tamnifolia* (L.) Griseb. (smallflower morningglory, IAQTA), *Ipomoea hederacea* (L.) Jacq. (ivyleaf morningglory, IPOHE), *Ipomoea lacunosa* L. (white morningglory, IPOLA), *Lactuca serriola* L./Torn. (prickly lettuce, LACSE), *Portulaca oleracea* L. (common purslane, POROL), *Richardia* species (pusley, RCHSS), *Sida* species (sida, SIDSS), *Sida spinosa* L. (prickly sida, SIDSP), *Sinapis arvensis* L. (wild mustard, SINAR), *Solanum ptychanthum* Dunal (eastern black nightshade, SOLPT), *Tridax procumbens* L. (coat buttons, TRQPR) or *Xanthium strumarium* L. (common cocklebur, XANST).

In some embodiments, the methods provided herein are utilized to control undesirable vegetation in turf. In certain embodiments, the undesirable vegetation is *Bellis perennis* L. (English daisy, BELPE), *Cyperus esculentus* L. (yellow nutsedge, CYPES), *Cyperus* species (CYPSS), *Digitaria sanguinalis* (L.) Scop. (large crabgrass, DIGSA), *Diodia virginiana* L. (Virginia buttonweed, DIQVI), *Euphorbia* species (spurge, EPHSS), *Glechoma hederacea* L. (ground ivy, GLEHE), *Hydrocotyle umbellata* L. (dollarweed, HYDUM), *Kyllinga* species (kyllinga, KYLSS), *Lamium amplexicaule* L. (henbit, LAMAM), *Murdannia nudiflora* (L.) Brenan (doveweed, MUDNU), *Oxalis* species (woodsorrel, OXASS), *Plantago major* L. (broadleaf plantain, PLAMA), *Plantago lanceolata* L. (buckhornlnarrowleaf plantain, PLALA), *Phyllanthus urinaria* L. (chamberbitter, PYLTE), *Rumex obtusifolius* L. (broadleaf dock, RUMOB), *Stachys floridana* Shuttlew. (Florida betony, STAFL), *Stellaria media* (L.) Vill. (common chickweed, STEME), *Taraxacum officinale* G. H. Weber ex Wiggers (dandelion, TAROF), *Trifolium repens* L. (white clover, TRFRE), or *Viola* species (wild violet, VIOSS).

In some embodiments, the compositions and methods provided herein are utilized to control undesirable vegetation, including grass, broadleaf and sedge weeds. In certain embodiments, the compositions and methods provided herein are utilized to control undesirable vegetation including but not limited to *Alopecurus, Avena, Centaurea, Cyperus, Digitaria, Echinochloa, Ipomoea, Leptochloa* and *Sonchus*.

In some embodiments, the combination of compound (I) or agriculturally acceptable ester or salt thereof and an imidazolinone or agriculturally acceptable salt or ester thereof is used to control *Alopecurus myosuroides* Huds. (blackgrass, ALOMY), *Avena fatua* L. (wild oat, AVEFA), *Centaurea biebersteinii* DC. (spotted knapweed, CENMA), *Cyperus esculentus* L. (yellow nutsedge, CYPES), *Cyperus iria* L. (rice flatsedge, CYPIR), *Digitaria sanguinalis* (L.) (Scop.) (large Crabgrass, DIGSA), *Echinochloa crus-galli* (L.) Beauv. (barnyardgrass, ECHCG), *Echinochloa colona* (L.) Link (junglerice, ECHCO), *Leptochloa chinensis* (L.) Nees (Chinese sprangletop, LEFCH), *Echinochloa oryzoides* (Ard.) Fritsch (early watergrass, ECHOR), *Ipomoea hederacea* Jacq. (ivyleaf morningglory, IPOHE) and *Sonchus arvensis* L. (perennial sowthistle, SONAR).

The compounds of formula I or agriculturally acceptable salt or ester thereof may be used to control herbicide resistant or tolerant weeds. The methods employing the combination of a compound of formula I or agriculturally acceptable salt or ester thereof and the compositions described herein may also be employed to control herbicide resistant or tolerant weeds. Exemplary resistant or tolerant weeds include, but are not limited to, biotypes resistant or tolerant to acetolactate synthase (ALS)) or acetohydroxy acid synthase (AHAS) inhibitors, (e.g., imidazolinones, sulfonylureas, pyrimidinylthiobenzoates, triazolopyrimidines, and sulfonylaminocarbonyltriazolinones), photosystem II inhibitors (e.g., phenylcarbamates, pyridazinones, triazines, triazinones, uracils, amides, ureas, benzothiadiazinones, nitriles, phenylpyridazines), acetyl CoA carboxylase (ACCase) inhibitors, (e.g., aryloxyphenoxypropionates, cyclohexanediones, phenylpyrazolines), synthetic auxins (e.g., benzoic acids, phenoxycarboxylic acids, pyridine carboxylic acids, quinoline carboxylic acids), auxin transport inhibitors (e.g., phthalamates, semicarbazones), photosystem I inhibitors (e.g., bipyridyliums), 5-enolpyruvylshikimate-3-phosphate (EPSP) synthase inhibitors (e.g., glyphosate), glutamine synthetase inhibitors (e.g., glufosinate, bialafos), microtubule assembly inhibitors (e.g., benzamides, benzoic acids, dinitroanilines, phosphoramidates, pyridines), mitosis inhibitors (e.g., carbamates), very long chain fatty acid (VLCFA) inhibitors (e.g., acetamides, chloroacetamides, oxyacetamides, tetrazolinones), fatty acid and lipid synthesis inhibitors (e.g., phosphorodithioates, thiocarbamates, benzofuranes, chlorocarbonic acids), protoporphyrinogen oxidase (PPO) inhibitors (e.g., diphenylethers, N-phenylphthalimides, oxadiazoles, oxazolidinediones, phenylpyrazoles, pyrimidindiones, thiadiazoles, triazolinones), carotenoid biosynthesis inhibitors (e.g., clomazone, amitrole, aclonifen), phytoene desaturase (PDS) inhibitors (e.g., amides, anilidex, furanones, phenoxybutan-amides, pyridiazinones, pyridines), 4-hydroxyphenyl-pyruvate-dioxygenase (HPPD) inhibitors (e.g., callistemones, isoxazoles, pyrazoles, triketones), cellulose biosynthesis inhibitors (e.g., nitriles, benzamides, quinclorac, triazolocarboxamides), herbicides with multiple modes-of-action such as quinclorac, and unclassified herbicides such as arylaminopropionic acids, difenzoquat, endothall, and organoarsenicals. Exemplary resistant or tolerant weeds include, but are not limited to, biotypes with resistance or tolerance to multiple herbicides, biotypes with resistance or tolerance to multiple chemical classes, biotypes with resistance or tolerance to multiple herbicide modes-of-action, and biotypes with multiple resistance or tolerance mechanisms (e.g., target site resistance or metabolic resistance).

In some embodiments, an agriculturally acceptable carboxylic acid, ester or salt of imazethapyr, imazamox, imazapic, imazapyr, imazamethabenz and imazaquin is employed in the methods or compositions described herein. In certain embodiments, the ammonium salt of imazethapyr, imazamox, or imazapic is employed. In certain embodiments, the isopropylammonium salt of imazapyr is employed.

In certain embodiments of the compositions and methods described herein, the compound of formula (I) or salt or ester thereof is used in combination with imazethapyr ammonium or salt or ester thereof. In some embodiments, the weight ratio of the compound of formula (I) or salt or ester thereof to imazethapyr or salt or ester thereof is within the range of from about 1:70 to about 29:1. In certain embodiments, the weight ratio of the compound of formula (I) or salt or ester thereof to imazethapyr or salt or ester thereof is within the range of from about 1:8 to about 2:1. In certain embodiments, the weight ratio of the compound of formula (I) or salt or ester thereof to imazethapyr or salt or ester thereof is within the range of from about 1:4.4 to about 2:1. In certain embodiments, the compositions provided herein comprise the compound of formula (I) or its benzyl or n-butyl ester and imazethapyr or its ammonium salt. In one embodiment, the composition comprises the compound of formula (I) and the imazethapyr ammonium, wherein the weight ratio of the compound of formula (I) to the imazethapyr ammonium is about 1:2.4 to about 2:1. In one embodiment, the composition comprises the benzyl ester of the compound of formula (I) and imazethapyr ammonium, wherein the weight ratio of the benzyl ester of the compound of formula (I) to imazethapyr ammonium is about 1:4 to about 2:1. In one embodiment, the composition comprises the n-butyl ester of the compound of formula (I) and imazethapyr ammonium, wherein the weight ratio of the n-butyl ester of the compound of formula (I) to imazethapyr ammonium is about 1:4.4. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 11 grams acid equivalent per hectare (gae/ha) to about 440 gae/ha based on the total amount of active ingredients in the composition. In certain embodiments, the composition is applied at an application rate of from about 45 grams acid equivalent per hectare (gae/ha) to about 340 gae/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and imazethapyr or salt or ester thereof, e.g., sequentially or simultaneously. In some embodiments, the imazethapyr or salt or ester thereof is applied at a rate from about 8.75 gae/ha to about 140 gae/ha and the compound of formula (I) of salt or ester thereof is applied at a rate from about 2 gae/ha to about 300 gae/ha. In some embodiments, the imazethapyr or salt or ester thereof is applied at a rate from about 4 gai/ha to about 140 gai/ha and the compound of formula (I) of salt or ester thereof is applied at a rate from about 4 g acid equivalent per hectare (gae/ha) to about 70 gae/ha. In some embodiments, the imazethapyr or salt or ester thereof is applied at a rate from about 8.75 gai/ha to about 70 gai/ha and the compound of formula (I) of salt or ester thereof is applied at a rate from about 8.75 g acid equivalent per hectare (gae/ha) to about 35 gae/ha. In certain embodiments, the methods utilize the compound of formula (I), or its benzyl or n-butyl ester and imazethapyr or its ammonium salt. In one embodiment, the methods utilize the compound of formula (I) and imazethapyr ammonium, wherein the compound of formula (I) is applied at a rate of from about 8.75 g acid equivalent per hectare (gae/ha) to about 35 gae/ha, and imazethapyr ammonium is applied at a rate of about 17.5 gai/ha to about 70 gai/ha. In one embodiment, the methods utilize the benzyl ester of the compound of formula (I) and imazethapyr ammonium, wherein the benzyl ester of the compound of formula (I) is applied at a rate of from about 8.75 g acid equivalent per hectare (gae/ha) to about 17.5 gae/ha, and imazethapyr ammonium is applied at a rate of about 8.75 gai/ha to about 35 gai/ha. In one embodiment, the methods utilize the n-butyl ester of the compound of formula (I) and imazethapyr ammonium, wherein the n-butyl ester of the compound of formula (I) is applied at a rate of about 16 g acid equivalent per hectare (gae/ha), and imazethapyr ammonium is applied at a rate of about 70 gai/ha. In certain embodiments, the methods and compositions utilizing the compound of formula (I) or salt or ester thereof in combination with imazethapyr or salt or ester thereof are used to control LEFCH, CYPES, DIGSA, ECHCG, ECHOR, or AVEFA.

In certain embodiments of the compositions and methods described herein, the compound of formula (I) or salt or ester thereof is used in combination with imazamox ammonium or salt or ester thereof. In some embodiments, the weight ratio of the compound of formula (I) or salt or ester thereof to imazamox or salt or ester thereof is within the range of from about 1:35 to about 45:1. In certain embodiments, the weight ratio of the compound of formula (I) or salt or ester thereof to imazethapyr or salt or ester thereof is within the range of from about 1:10 to about 3:1. In certain embodiments, the weight ratio of the compound of formula (I) or salt or ester thereof to imazamox or salt thereof is within the range of from about 1:10 to about 12:1. In certain embodiments, the weight ratio of the compound of formula (I) or salt or ester thereof to imazamox or salt or ester thereof is within the range of from about 1:5.1 to about 6.3:1. In certain embodiments, the compositions provided herein comprise the compound of formula (I) or its benzyl and the ammonium salt of imazamox. In one embodiment, the composition comprises the compound of formula (I) and imazamox ammonium, wherein the weight ratio of the compound of formula (I) to imazamox ammonium is about 1:5.1 to about 3.1:1. In one embodiment, the composition comprises the benzyl ester of the compound of formula (I) and imazamox ammonium, wherein the weight ratio of the benzyl ester of the compound of formula (I) to imazamox ammonium is about 1:2.6 to about 6.3:1. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 7.6 grams acid equivalent per hectare (gae/ha) to about 370 gae/ha based on the total amount of active ingredients in the composition. In certain embodiments, the composition is applied at an application rate of from about 50 grams acid equivalent per hectare (gae/ ha) to about 270 gae/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and imazamox or salt or ester thereof, e.g., sequentially or simultaneously. In some embodiments, the imazamox or salt or ester thereof is applied at a rate from about 5.6 gae/ha to about 70 gae/ha and compound of formula (I) or salt or ester thereof is applied at a rate from about 2 gae/ha to about 300 gae/ha. In some embodiments, the imazamox or salt or ester thereof is applied at a rate from about 2 gai/ha to about 90 gai/ha and the compound of formula (I) of salt or ester thereof is applied at a rate from about 2 g acid equivalent per hectare (gae/ha) to about 70 gae/ha. In some embodiments, the imazamox or salt or ester thereof is applied at a rate from about 5.6 gai/ha to about 44.8 gai/ha and the compound of formula (I) of salt or ester thereof is applied at a rate from about 4.38 g acid equivalent per hectare (gae/ha) to about 35 gae/ha. In certain embodiments, the methods utilize the compound of formula (I), or its benzyl ester and the ammonium salt of imazamox or its ammonium salt. In one embodiment, the methods utilize the compound of formula (I) and imazamox ammonium, wherein the compound of formula (I) is applied at a rate of from about 4.38 g acid equivalent per hectare (gae/ha) to about 35 gae/ha, and imazamox ammonium is applied at a rate of about 5.6 gai/ha to about 44.8 gai/ha. In one embodiment, the methods utilize the benzyl ester of the compound of formula (I) and imazamox ammonium, wherein the benzyl ester of the compound of formula (I) is applied at a rate of from about 4.38 g acid equivalent per hectare (gae/ha) to about 35 gae/ha, and imazamox ammonium is applied at a rate of about 5.6 gai/ha to about 22.4 gai/ha. In certain embodiments, the methods and compositions utilizing the compound of formula (I) or salt or ester thereof in combination with imazamox or salt or ester thereof are used to control ECHCG, CYPES, LEFCH, DIGSA, CYPIR, or ECHOR.

In certain embodiments of the compositions and methods described herein, the compound of formula (I) or salt or ester thereof is used in combination with imazapic ammonium or salt or ester thereof. In some embodiments, the weight ratio of the compound of formula (I) or salt or ester thereof to imazapic or salt or ester thereof is within the range of from about 1:105 to about 5:1. In certain embodiments, the weight ratio of the compound of formula (I) or salt or ester thereof to imazapic or salt or ester thereof is within the range of from about 1:16 to about 8:1. In certain embodiments, the weight ratio of the compound of formula (I) or salt or ester thereof to imazapic or salt or ester thereof is within the range of from about 1:8 to about 8:1. In certain embodiments, the weight ratio of the compound of formula (I) or salt or ester thereof to imazapic or salt or ester thereof is within the range of from about 1:4 to about 4:1. In certain embodiments, the compositions provided herein comprise the compound of formula (I) or its benzyl ester and imazapic. In one embodiment, the composition comprises the compound of formula (I) and imazapic, wherein the weight ratio of the compound of formula (I) to imazapic is about 1:4 to about 2:1. In one embodiment, the composition comprises the benzyl ester of the compound of formula (I) and the ammonium salt of imazapic, wherein the weight ratio of the benzyl ester of the compound of formula (I) to imazapic is about 1:2 to about 4:1. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 6.0 grams acid equivalent per hectare (gae/ha) to about 510 gae/ha based on the total amount of active ingredients in the composition. In certain embodiments, the composition is applied at an application rate of from about 75 grams acid equivalent per hectare (gae/ha) to about 270 gae/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and imazapic or salt or ester thereof, e.g., sequentially or simultaneously. In some embodiments, the imazapic or salt or ester thereof is applied at a rate from about 4.4 gae/ha to about 210 gae/ha and the compound of formula (I) or salt or ester thereof is applied at a rate from about 2 gae/ha to about 300 gae/ha. In some embodiments, the imazapic or salt or ester thereof is applied at a rate from about 2 gai/ha to about 70 gai/ha and the compound of formula (I) of salt or ester thereof is applied at a rate from about 2 g acid equivalent per hectare (gae/ha) to about 45 gae/ha. In some embodiments, the imazapic or salt or ester thereof is applied at a rate from about 4.38 gai/ha to about 35 gai/ha and the compound of formula (I) of salt or ester thereof is applied at a rate from about 4.38 g acid equivalent per hectare (gae/ha) to about 42 gae/ha. In certain embodiments, the methods utilize the compound of formula (I), or its benzyl ester and imazapic. In one embodiment, the methods utilize the compound of formula (I) and imazapic, wherein the compound of formula (I) is applied at a rate of from about 4.38 g acid equivalent per hectare (gae/ha) to about 42 gae/ha, and imazapic is applied at a rate of about 4.38 gai/ha to about 35 gai/ha. In one embodiment, the methods utilize the benzyl ester of the compound of formula (I) and imazapic, wherein the benzyl ester of the compound of formula (I) is applied at a rate of from about 8.75 g acid equivalent per hectare (gae/ha) to about 35 gae/ha, and imazapic is applied at a rate of about 4.38 gai/ha to about 17.5 gai/ha. In certain embodiments, the methods and compositions utilizing the compound of formula (I) or salt or ester thereof in combination with imazapic or salt or ester thereof are used to control CYPIR, ECHCG, ECHCO, LEFCH, ECHOR, ALOMY, AVEFA, CENMA, or SONAR.

In certain embodiments of the compositions and methods described herein, the compound of formula (I) or salt or ester thereof is used in combination with imazapyr isopropylamine or salt or ester thereof. In some embodiments, the weight ratio of the compound of formula (I) or salt or ester thereof to imazapyr or salt or ester thereof lies within the range of from about 1:750 to about 3:1. In certain embodiments, the weight ratio of the compound of formula (I) or salt or ester thereof to imazapyr or salt or ester thereof is within the range of from about 1:64 to about 1:3. In certain embodiments, the weight ratio of the compound of formula (I) or salt or ester thereof to imazapyr or salt or ester thereof is within the range of from about 1:26 to about 8:1. In certain embodiments, the weight ratio of the compound of formula (I) or salt or ester thereof to imazapyr or salt or ester thereof is within the range of from about 1:13.2 to about 4:1. In certain embodiments, the compositions provided herein comprise the compound of formula (I) or its benzyl or n-butyl ester and imazapyr or its isopropylammonium salt. In one embodiment, the composition comprises the compound of formula (I) and imazapyr isopropylammonium, wherein the weight ratio of the compound of formula (I) to imazapyr isopropylammonium is about 1:13.2 to about 4:1. In one embodiment, the composition comprises the benzyl ester of the compound of formula (I) and imazapyr isopropylammonium, wherein the weight ratio of the benzyl ester of the compound of formula (I) to imazapyr isopropylammonium is about 1:8 to about 4:1. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 100 grams active ingredient per hectare (gai/ha) to about 1800 gai/ha based on the total amount of active ingredients in the composition. In certain embodiments, the composition is applied at an application rate of from about 140 grams active ingredient per hectare (gai/ha) to about 610 gai/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and imazapyr or salt or ester thereof, e.g., sequentially or simultaneously. In some embodiments, the imazapyr or salt or ester thereof is applied at a rate from about 100 gai/ha to about 1500 gai/ha and the compound of formula (I) or salt or ester thereof is applied at a rate from about 2 gae/ha to about 300 gae/ha. In some embodiments, the imazapyr or salt or ester thereof is applied at a rate from about 2 gai/ha to about 300 gai/ha and the compound of formula (I) of salt or ester thereof is applied at a rate from about 2 g acid equivalent per hectare (gae/ha) to about 100 gae/ha. In some embodiments, the imazapyr or salt or ester thereof is applied at a rate from about 4.38 gai/ha to about 140 gai/ha and the compound of formula (I) of salt or ester thereof is applied at a rate from about 4.38 g acid equivalent per hectare (gae/ha) to about 42.4 gae/ha. In certain embodiments, the methods utilize the compound of formula (I), or its benzyl or n-butyl ester and imazapyr or its isopropylammonium salt. In one embodiment, the methods utilize the compound of formula (I) and imazapyr isopropylammonium, wherein the compound of formula (I) is applied at a rate of from about 4.38 g acid equivalent per hectare (gae/ha) to about 42.4 gae/ha, and imazapyr isopropylammonium is applied at a rate of about 4.38 gai/ha to about 140 gai/ha. In one embodiment, the methods utilize the benzyl ester of the compound of formula (I) and imazapyr isopropylammonium, wherein the benzyl ester of the compound of formula (I) is applied at a rate of from about 4.38 g acid equivalent per hectare (gae/ha) to about 17.5 gae/ha, and imazapyr isopropylammonium is applied at a rate of about 4.38 gai/ha to about 140 gai/ha. In certain embodiments, the methods and compositions utilizing the compound of formula (I) or salt or ester thereof in combination with imazapyr or salt or ester thereof are used to control IPOHE, ECHOR, or CYPRO.

In certain embodiments of the compositions and methods described herein, the compound of formula (I) or salt or ester thereof is used in combination with imazamethabenz-methyl or salt or ester thereof. With regard to the compositions, in some embodiments, the weight ratio of the compound of formula (I) or salt or ester thereof to imazamethabenz-methyl or salt or ester thereof is within the range of from about 1:350 to about 1.5:1. In certain embodiments, the weight ratio of the compound of formula (I) or salt or ester thereof imazamethabenz-methyl or salt or ester thereof is within the range of from about 1:200 to about 10:1. In certain embodiments, the compositions comprise the compound of formula (I) or its benzyl or n-butyl ester and imazamethabenz-methyl. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 200 grams acid equivalent per hectare (gae/ha) to about 1,000 gae/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and imazamethabenz-methyl or salt or ester thereof, e.g., sequentially or simultaneously. In certain embodiments, the composition is applied at an application rate of from about 350 grams acid equivalent per hectare (gae/ha) to about 800 gae/ha based on the total amount of active ingredients in the composition. In some embodiments, imazamethabenz-methyl or salt or ester thereof is applied at a rate from about 200 gae/ha to about 700 gae/ha and the compound of formula (I) or salt or ester thereof is applied at a rate from about 2 gae/ha to about 300 gae/ha. In certain embodiments, the methods utilize the compound of formula (I) or its benzyl or n-butyl ester and imazamethabenz-methyl. In certain embodiments, the methods and compositions utilizing the compound of formula (I) or salt or ester thereof in combination with imazamethabenz-methyl or salt or ester thereof are used to control CHEAL, CIRAR, CYPIR, PAPRH, SASKR, SINAR and VERPE.

In certain embodiments of the compositions and methods described herein, the compound of formula (I) or salt or ester thereof is used in combination with imazamethabenz-methyl or salt or ester thereof. In some embodiments, the weight ratio of the compound of formula (I) or salt or ester thereof to imazamethabenz-methyl or salt or ester thereof is within the range of from about 1:350 to about 1.5:1. In certain embodiments, the weight ratio of the compound of formula (I) or salt or ester thereof imazamethabenz-methyl or salt or ester thereof is within the range of from about 1:100 to about 1:5. In certain embodiments, the compositions comprise the compound of formula (I) or its benzyl or n-butyl ester and imazamethabenz-methyl. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 200 grams acid equivalent per hectare (gae/ha) to about 1,000 gae/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and imazamethabenz-methyl or salt or ester thereof, e.g., sequentially or simultaneously. In certain embodiments, the composition is applied at an application rate of from about 350 grams acid equivalent per hectare (gae/ha) to about 800 gae/ha based on the total amount of active ingredients in the composition. In special embodiments, the composition is applied at an application rate of from about 200 grams acid equivalent per hectare (gae/ha) to about 550 gae/ha based on the total amount of active ingredients in the composition. In special embodiments, the composition is applied at an application rate of from about 46 grams acid equivalent per hectare (gae/ha) to about 208 gae/ha based on the total amount of active ingredients in the composition. In some embodiments, imazamethabenz-methyl or salt or ester thereof is applied at a rate from about 10 gae/ha to about 700 gae/ha and the compound of formula (I) or salt or ester thereof is applied at a rate from about 0.5 gae/ha to about 300 gae/ha. In special embodiments, imazamethabenz-methyl or salt or ester thereof is applied at a rate from about 20 gae/ha to about 500 gae/ha and the compound of formula (I) or salt or ester thereof is applied at a rate from about 1 gae/ha to about 100 gae/ha. In special embodiments, imazamethabenz-methyl or salt or ester thereof is applied at a rate from about 44 gae/ha to about 200 gae/ha and the compound of formula (I) or salt or ester thereof is applied at a rate from about 2 gae/ha to about 8 gae/ha. In certain embodiments, the methods utilize the compound of formula (I) or its benzyl or n-butyl ester and imazamethabenz-methyl. In certain embodiments, the methods and compositions utilizing the compound of formula (I) or salt or ester thereof in combination with imazamethabenz-methyl or salt or ester thereof are used to control CHEAL, CIRAR, CYPIR, PAPRH, SASKR, SINAR and VERPE.

In certain embodiments of the compositions and methods described herein, the compound of formula (I) or salt or ester thereof is used in combination with imazaquin isopropylamine or salt or ester thereof. In some embodiments, the weight ratio of the compound of formula (I) or salt or ester thereof to imazaquin or salt or ester thereof is within the range of from about 1:105 to about 8:1. In certain embodiments, the weight ratio of the compound of formula (I) or salt or ester thereof to imazaquin or salt or ester thereof is within the range of from about 1:10 to about 4:1. In certain embodiments, the weight ratio of the compound of formula (I) or salt or ester thereof to imazaquin or salt or ester thereof is within the range of from about 1:20 to about 4:1. In certain embodiments, the weight ratio of the compound of formula (I) or salt or ester thereof to imazaquin or salt or ester thereof is within the range of from about 1:8.2 to about 1.9:1. In certain embodiments, the compositions provided herein comprise the compound of formula (I) or its benzyl ester and imazaquin. In one embodiment, the composition comprises the compound of formula (I) and imazaquin, wherein the weight ratio of the compound of formula (I) to imazaquin is about 1:2 to about 1.9:1. In one embodiment, the composition comprises the benzyl ester of the compound of formula (I) and imazaquin, wherein the weight ratio of the benzyl ester of the compound of formula (I) to the imazaquin is about 1:8.2 to about 1:2. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 6.0 grams acid equivalent per hectare (gae/ha) to about 510 gae/ha based on the total amount of active ingredients in the composition. In certain embodiments, the composition is applied at an application rate of from about 12 grams acid equivalent per hectare (gae/ha) to about 180 gae/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and imazaquin or salt or ester thereof, e.g., sequentially or simultaneously. In some embodiments, imazaquin or salt or ester thereof is applied at a rate from about 4.4 gae/ha to about 210 gae/ha and the compound of formula (I) or salt or ester thereof is applied at a rate from about 2 gae/ha to about 300 gae/ha. In some embodiments, the imazaquin or salt or ester thereof is applied at a rate from about 4 gai/ha to about 80 gai/ha and the compound of formula (I) of salt or ester thereof is applied at a rate from about 2 g acid equivalent per hectare (gae/ha) to about 40 gae/ha. In some embodiments, the imazaquin or salt or ester thereof is applied at a rate from about 9 gai/ha to about 36 gai/ha and the compound of formula (I) of salt or ester thereof is applied at a rate from about 4.38 g acid equivalent per hectare (gae/ha) to about 17.5 gae/ha. In certain embodiments, the methods utilize the compound of formula (I), or its benzyl ester and imazaquin. In one embodiment, the methods utilize the compound of formula (I) and imazaquin, wherein the compound of formula (I) is applied at a rate of from about 4.38 g acid equivalent per hectare (gae/ha) to about 17.5 ae/ha, and imazaquin is applied at a rate of about 9 gai/ha. In one embodiment, the methods utilize the benzyl ester of the compound of formula (I) and imazaquin, wherein the benzyl ester of the compound of formula (I) is applied at a rate of from about 4.38 g acid equivalent per hectare (gae/ha) to about 8.75 gae/ha, and imazaquin is applied at a rate of about 18 gai/ha to about 36 gai/ha. In certain embodiments, the methods and compositions utilizing the compound of formula (I) or salt or ester thereof in combination with imazaquin or salt or ester thereof are used to control IPOHE.

The components of the mixtures described herein can be applied either separately or as part of a multipart herbicidal system.

The mixtures described herein can be applied in conjunction with one or more other herbicides to control a wider variety of undesirable vegetation. When used in conjunction with other herbicides, the composition can be formulated with the other herbicide or herbicides, tank mixed with the other herbicide or herbicides or applied sequentially with the other herbicide or herbicides. Some of the herbicides that can be employed in conjunction with the compositions and methods described herein include, but are not limited to: 4-CPA; 4-CPB; 4-CPP; 2,4-D; 2,4-D choline salt, 2,4-D esters and amines, 2,4-DB; 3,4-DA; 3,4-DB; 2,4-DEB; 2,4-DEP; 3,4-DP; 2,3,6-TBA; 2,4,5-T; 2,4,5-TB; acetochlor, acifluorfen, aclonifen, acrolein, alachlor, allidochlor, alloxydim, allyl alcohol, alorac, ametridione, ametryn, amibuzin, amicarbazone, amidosulfuron, aminocyclopyrachlor, aminopyralid, amiprofos-methyl, amitrole, ammonium sulfamate, anilofos, anisuron, asulam, atraton, atrazine, azafenidin, azimsulfuron, aziprotryne, barban, BCPC, beflubutamid, benazolin, bencarbazone, benfluralin, benfuresate, bensulfuron-methyl, bensulide, benthiocarb, bentazon-sodium, benzadox, benzfendizone, benzipram, benzobicyclon, benzofenap, benzofluor, benzoylprop, benzthiazuron, bialaphos, bicyclopyrone, bifenox, bilanafos, bispyribac-sodium, borax, bromacil, bromobonil, bromobutide, bromofenoxim, bromoxynil, brompyrazon, butachlor, butafenacil, butamifos, butenachlor, buthidazole, buthiuron, butralin, butroxydim, buturon, butylate, cacodylic acid, cafenstrole, calcium chlorate, calcium cyanamide, cambendichlor, carbasulam, carbetamide, carboxazole chlorprocarb, carfentrazone-ethyl, CDEA, CEPC, chlomethoxyfen, chloramben, chloranocryl, chlorazifop, chlorazine, chlorbromuron, chlorbufam, chloreturon, chlorfenac, chlorfenprop, chlorflurazole, chlorflurenol, chloridazon, chlorimuron, chlornitrofen, chloropon, chlorotoluron, chloroxuron, chloroxynil, chlorpropham, chlorsulfuron, chlorthal, chlorthiamid, cinidon-ethyl, cinmethylin, cinosulfuron, cisanilide, clethodim, cliodinate, clodinafop-propargyl, clofop, clomazone, clomeprop, cloprop, cloproxydim, clopyralid, cloransulam-methyl, CMA, copper sulfate, CPMF, CPPC, credazine, cresol, cumyluron, cyanatryn, cyanazine, cycloate, cyclopyrimorate, cyclosulfamuron, cycloxydim, cycluron, cyhalofop-butyl, cyperquat, cyprazine, cyprazole, cypromid, daimuron, dalapon, dazomet, delachlor, desmedipham, desmetryn, di-allate, dicamba, dichlobenil, dichloralurea, dichlormate, dichlorprop, dichlorprop-P, diclofop-methyl, diclosulam, diethamquat, diethatyl, difenopenten, difenoxuron, difenzoquat, diflufenican, diflufenzopyr, dimefuron, dimepiperate, dimethachlor, dimethametryn, dimethenamid, dimethenamid-P, dimexano, dimidazon, dinitramine, dinofenate, dinoprop, dinosam, dinoseb, dinoterb, diphenamid, dipropetryn, diquat, disul, dithiopyr, diuron, DMPA, DNOC, DSMA, EBEP, eglinazine, endothal, epronaz, EPTC, erbon, esprocarb, ethalfluralin, ethbenzamide, ethametsulfuron, ethidimuron, ethiolate, ethobenzamid, etobenzamid, ethofumesate, ethoxyfen, ethoxysulfuron, etinofen, etnipromid, etobenzanid, EXD, fenasulam, fenoprop, fenoxaprop, fenoxaprop-P-ethyl, fenoxaprop-P-ethyl+isoxadifen-ethyl, fenoxasulfone, fenteracol, fenthiaprop, fentrazamide, fenuron, ferrous sulfate, flamprop, flamprop-M, flazasulfuron, florasulam, fluazifop, fluazifop-P-butyl, fluazolate, flucarbazone, flucetosulfuron, fluchloralin, flufenacet, flufenican, flufenpyr-ethyl, flumetsulam, flumezin, flumiclorac-pentyl, flumioxazin, flumipropyn, fluometuron, fluorodifen, fluoroglycofen, fluoromidine, fluoronitrofen, fluothiuron, flupoxam, flupropacil, flupropanate, flupyrsulfuron, fluridone, fluorochloridone, fluoroxypyr, fluoroxypyr-meptyl, flurtamone, fluthiacet, fomesafen, foramsulfuron, fosamine, fumiclorac, furyloxyfen, glufosinate, glufosinate-ammonium, glufosinate-P-ammonium, glyphosate salts and esters, halosafen, halauxifen, halauxifen-methyl, halosulfuron-methyl, haloxydine, haloxyfop-methyl, haloxyfop-P-methyl, hexachloroacetone, hexaflurate, hexazinone, imazosulfuron, indanofan, indaziflam, iodobonil, iodomethane, iodosulfuron, iodosulfuron-ethyl-sodium, iofensulfuron, ioxynil, ipazine, ipfencarbazone, iprymidam, isocarbamid, isocil, isomethiozin, isonoruron, isopolinate, isopropalin, isoproturon, isouron, isoxaben, isoxachlortole, isoxaflutole, isoxapyrifop, karbutilate, ketospiradox, lactofen, lenacil, linuron, MAA, MAMA, MCPA esters and amines, MCPA-thioethyl, MCPB, mecoprop, mecoprop-P, medinoterb, mefenacet, mefluidide, mesoprazine, mesosulfuron, mesotrione, metam, metamifop, metamitron, metazachlor, metazosulfuron, metflurazon, methabenzthiazuron, methalpropalin, methazole, methiobencarb, methiozolin, methiuron, methometon, methoprotryne, methyl bromide, methyl isothiocyanate, methyldymron, metobenzuron, metobromuron, metolachlor, metosulam, metoxuron, metribuzin, metsulfuron, metsulfuron-methyl, molinate, monalide, monisouron, monochloroacetic acid, monolinuron, monuron, morfamquat, MSMA, naproanilide, napropamide, naptalam, neburon, nicosulfuron, nipyraclofen, nitralin, nitrofen, nitrofluorfen, norflurazon, noruron, OCH, orbencarb, ortho-dichlorobenzene, orthosulfamuron, oryzalin, oxadiargyl, oxadiazon, oxapyrazon, oxasulfuron, oxaziclomefone, oxyfluorfen, paraflufenethyl, parafluoron, paraquat, pebulate, pelargonic acid, pendimethalin, penoxsulam, pentachlorophenol, pentanochlor, pentoxazone, perfluidone, pethoxamid, phenisopham, phenmedipham, phenmedipham-ethyl, phenobenzuron, phenylmercury acetate, picloram, picolinafen, pinoxaden, piperophos, potassium arsenite, potassium azide, potassium cyanate, pretilachlor, primisulfuron-methyl, procyazine, prodiamine, profluazol, profluralin, profoxydim, proglinazine, prohexadione-calcium, prometon, prometryn, pronamide, propachlor, propanil, propaquizafop, propazine, propham, propisochlor, propoxycarbazone, propyrisulfuron, propyzamide, prosulfalin, prosulfocarb, prosulfuron, proxan, prynachlor, pydanon, pyraclonil, pyraflufen-ethyl, pyrasulfotole, pyrazogyl, pyrazolynate, pyrazosulfuron-ethyl, pyrazoxyfen, pyribenzoxim, pyributicarb, pyriclor, pyridafol, pyridate, pyriftalid, pyriminobac-methyl, pyrimisulfan, pyrithiobac-sodium, pyroxasulfone, pyroxsulam, quinclorac, quinmerac, quinoclamine, quinonamid, quizalofop, quizalofop-P-ethyl, rhodethanil, rimsulfuron, saflufenacil, S-metolachlor, sebuthylazine, secbumeton, sethoxydim, siduron, simazine, simeton, simetryn, SMA, sodium arsenite, sodium azide, sodium chlorate, sulcotrione, sulfallate, sulfentrazone, sulfometuron, sulfosate, sulfosulfuron, sulfuric acid, sulglycapin, swep, SYN-523, TCA, tebutam, tebuthiuron, tefuryltrione, tembotrione, tepraloxydim, terbacil, terbucarb, terbuchlor, terbumeton, terbuthylazine, terbutryn, tetrafluoron, thenylchlor, thiazafluoron, thiazopyr, thidiazimin, thidiazuron, thiencarbazone-methyl, thifensulfuron, thifensulfurn-methyl, thiobencarb, tiocarbazil, tioclorim, topramezone, tralkoxydim, triafamone, tri-allate, triasulfuron, triaziflam, tribenuron, tribenuron-methyl, tricamba, triclopyr choline salt, triclopyr esters and amines, tridiphane, trietazine, trifloxysulfuron, trifluralin, triflusulfuron, trifop, trifopsime, trihydroxytriazine, trimeturon, tripropindan, tritac tritosulfuron, vernolate, xylachlor and salts, esters, optically active isomers and mixtures thereof.

The compositions and methods described herein, can further be used in conjunction with glyphosate, 5-enolpyruvylshikimate-3-phosphate (EPSP) synthase inhibitors, glufosinate, glutamine synthetase inhibitors, dicamba, phenoxy auxins, pyridyloxy auxins, synthetic auxins, auxin transport inhibitors, aryloxyphenoxypropionates, cyclohexanediones, phenylpyrazolines, acetyl CoA carboxylase (ACCase) inhibitors, imidazolinones, sulfonylureas, pyrimidinylthiobenzoates, triazolopyrimidines, sulfonylaminocarbonyltriazolinones, acetolactate synthase (ALS) or acetohydroxy acid synthase (AHAS) inhibitors, 4-hydroxyphenyl-pyruvate dioxygenase (HPPD) inhibitors, phytoene desaturase inhibitors, carotenoid biosynthesis inhibitors, protoporphyrinogen oxidase (PPO) inhibitors, cellulose biosynthesis inhibitors, mitosis inhibitors, microtubule inhibitors, very long chain fatty acid inhibitors, fatty acid and lipid biosynthesis inhibitors, photosystem I inhibitors, photosystem II inhibitors, triazines, and bromoxynil on glyphosate-tolerant, EPSP synthase inhibitor-tolerant, glufosinate-tolerant, glutamine synthetase inhibitor-tolerant, dicamba-tolerant, phenoxy auxin-tolerant, pyridyloxy auxin-tolerant, auxin-tolerant, auxin transport inhibitor-tolerant, aryloxyphenoxypropionate-tolerant, cyclohexanedione-tolerant, phenylpyrazoline-tolerant, ACCase-tolerant, imidazolinone-tolerant, sulfonylurea-tolerant, pyrimidinylthiobenzoate-tolerant, triazolopyrimidine-tolerant, sulfonylaminocarbonyltriazolinone-tolerant, ALS- or AHAS-tolerant, HPPD-tolerant, phytoene desaturase inhibitor-tolerant, carotenoid biosynthesis inhibitor tolerant, PPO-tolerant, cellulose biosynthesis inhibitor-tolerant, mitosis inhibitor-tolerant, microtubule inhibitor-tolerant, very long chain fatty acid inhibitor-tolerant, fatty acid and lipid biosynthesis inhibitor-tolerant, photosystem I inhibitor-tolerant, photosystem II inhibitor-tolerant, triazine-tolerant, and bromoxynil-tolerant crops, and crops possessing multiple or stacked traits conferring tolerance to multiple chemistries and/or multiple modes of action via single and/or multiple resistance mechanisms. In some embodiments, the compound of formula (I) or salt or ester thereof and complementary herbicide or salt or ester thereof are used in combination with herbicides that are selective for the crop being treated and which complement the spectrum of weeds controlled by these compounds at the application rate employed. In some embodiments, the compositions described herein and other complementary herbicides are applied at the same time, either as a combination formulation or as a tank mix or as a sequential application.

In some embodiments, the compositions described herein are employed in combination with one or more herbicide safeners, such as AD-67 (MON 4660), benoxacor, benthiocarb, brassinolide, cloquintocet (mexyl), cyometrinil, daimuron, dichlormid, dicyclonon, dimepiperate, disulfoton, fenchlorazole-ethyl, fenclorim, flurazole, fluxofenim, furilazole, harpin proteins, isoxadifen-ethyl, jiecaowan, jiecaoxi, mefenpyr-diethyl, mephenate, naphthalic anhydride (NA), oxabetrinil, R29148 and N-phenyl-sulfonylbenzoic acid amides, to enhance their selectivity. In some embodiments, the safeners are employed in rice, cereal, corn, or maize settings. In some embodiments, the safener is cloquintocet or an ester or salt thereof. In certain embodiments, cloquintocet is utilized to antagonize harmful effects of the compositions on rice and cereals. In some embodiments, the safener is cloquintocet (mexyl).

In some embodiments, the compositions described herein are employed in combination with one or more plant growth regulators, such as 2,3,5-tri-iodobenzoic acid, IAA, IBA, naphthaleneacetamide, α-naphthaleneacetic acids, benzyladenine, 4-hydroxyphenethyl alcohol, kinetin, zeatin, endothal, ethephon, pentachlorophenol, thidiazuron, tribufos, aviglycine, ethephon, maleic hydrazide, gibberellins, gibberellic acid, abscisic acid, ancymidol, fosamine, glyphosine, isopyrimol, jasmonic acid, maleic hydrazide, mepiquat, 2,3,5-tri-iodobenzoic acid, morphactins, dichlorflurenol, flurprimidol, mefluidide, paclobutrazol, tetcyclacis, uniconazole, brassinolide, brassinolide-ethyl, cycloheximide, ethylene, methasulfocarb, prohexadione, triapenthenol and trinexapac.

In some embodiments, the plant growth regulators are employed in one or more crops or settings, such as rice, cereal crops, corn, maize, broadleaf crops, oilseed rape/canola, turf, pineapple, sugarcane, sunflower, pastures, grasslands, rangelands, fallowland, tree and vine orchards, plantation crops, vegetables, and non-crop (ornamentals) settings. In some embodiments, the plant growth regulator is mixed with the compound of formula (I), or mixed with the compound of formula (I) and an imidazolinone to cause a preferentially advantageous effect on plants.

In some embodiments, compositions provided herein further comprise at least one agriculturally acceptable adjuvant or carrier. Suitable adjuvants or carriers should not be phytotoxic to valuable crops, particularly at the concentrations employed in applying the compositions for selective weed control in the presence of crops, and should not react chemically with herbicidal components or other composition ingredients. Such mixtures can be designed for application directly to weeds or their locus or can be concentrates or formulations that are normally diluted with additional carriers and adjuvants before application. They can be solids, such as, for example, dusts, granules, water-dispersible granules, or wettable powders, or liquids, such as, for example, emulsifiable concentrates, solutions, emulsions or suspensions. They can also be provided as a pre-mix or tank mixed.

Suitable agricultural adjuvants and carriers include, but are not limited to, crop oil concentrate; nonylphenol ethoxylate; benzylcocoalkyldimethyl quaternary ammonium salt; blend of petroleum hydrocarbon, alkyl esters, organic acid, and anionic surfactant; $C_9$-$C_{11}$ alkylpolyglycoside; phosphated alcohol ethoxylate; natural primary alcohol ($C_{12}$-$C_{16}$) ethoxylate; di-sec-butylphenol EO-PO block copolymer; polysiloxane-methyl cap; nonylphenol ethoxylate+urea ammonium nitrate; emulsified methylated seed oil; tridecyl alcohol (synthetic) ethoxylate (8 EO); tallow amine ethoxylate (15 EO); PEG (400) dioleate-99.

Liquid carriers that can be employed include water and organic solvents. The organic solvents include, but are not limited to, petroleum fractions or hydrocarbons such as mineral oil, aromatic solvents, paraffinic oils, and the like; vegetable oils such as soybean oil, rapeseed oil, olive oil, castor oil, sunflower seed oil, coconut oil, corn oil, cottonseed oil, linseed oil, palm oil, peanut oil, safflower oil, sesame oil, tung oil and the like; esters of the above vegetable oils; esters of monoalcohols or dihydric, trihydric, or other lower polyalcohols (4-6 hydroxy containing), such as 2-ethyl hexyl stearate, n-butyl oleate, isopropyl myristate, propylene glycol dioleate, di-octyl succinate, di-butyl adipate, di-octyl phthalate and the like; esters of mono, di and polycarboxylic acids and the like. Specific organic solvents include, but are not limited to toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methyl alcohol, ethyl alcohol, isopropyl alcohol, amyl alcohol, ethylene glycol, propylene glycol, glycerine, N-methyl-2-pyrrolidinone, N,N-dimethyl alkylamides, dimethyl sulfoxide, liquid fertilizers and the like. In certain embodiments, water is the carrier for the dilution of concentrates.

Suitable solid carriers include but are not limited to talc, pyrophyllite clay, silica, attapulgus clay, kaolin clay, kieselguhr, chalk, diatomaceous earth, lime, calcium carbonate, bentonite clay, Fuller's earth, cottonseed hulls, wheat flour, soybean flour, pumice, wood flour, walnut shell flour, lignin, cellulose, and the like.

In some embodiments, the compositions described herein further comprise one or more surface-active agents. In some embodiments, such surface-active agents are employed in both solid and liquid compositions, and in certain embodiments those designed to be diluted with carrier before application. The surface-active agents can be anionic, cationic or nonionic in character and can be employed as emulsifying agents, wetting agents, suspending agents, or for other purposes. Surfactants which may also be used in the present formulations are described, inter alia, in "McCutcheon's Detergents and Emulsifiers Annual," MC Publishing Corp., Ridgewood, N.J., 1998 and in "Encyclopedia of Surfactants," Vol. I-III, Chemical Publishing Co., New York, 1980-81. Surface-active agents include, but are not limited to salts of alkyl sulfates, such as diethanolammonium lauryl sulfate; alkylarylsulfonate salts, such as calcium dodecylbenzenesulfonate; alkylphenol-alkylene oxide addition products, such as nonylphenol-$C_{18}$ ethoxylate; alcohol-alkylene oxide addition products, such as tridecyl alcohol-$C_{16}$ ethoxylate; soaps, such as sodium stearate; alkyl-naphthalene-sulfonate salts, such as sodium dibutylnaphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; salts of mono and dialkyl phosphate esters; vegetable or seed oils such as soybean oil, rapeseed/canola oil, olive oil, castor oil, sunflower seed oil, coconut oil, corn oil, cottonseed oil, linseed oil, palm oil, peanut oil, safflower oil, sesame oil, tung oil and the like; and esters of the above vegetable oils, and in certain embodiments, methyl esters.

In some embodiments, these materials, such as vegetable or seed oils and their esters, can be used interchangeably as an agricultural adjuvant, as a liquid carrier or as a surface active agent.

Other exemplary additives for use in the compositions provided herein include but are not limited to compatibilizing agents, antifoam agents, sequestering agents, neutralizing agents and buffers, corrosion inhibitors, dyes, odorants, spreading agents, penetration aids, sticking agents, dispersing agents, thickening agents, freezing point depressants, antimicrobial agents, and the like. The compositions may also contain other compatible components, for example, other herbicides, plant growth regulators, fungicides, insecticides, and the like and can be formulated with liquid fertilizers or solid, particulate fertilizer carriers such as ammonium nitrate, urea and the like.

In some embodiments, the concentration of the active ingredients in the compositions described herein is from about 0.0005 to 98 percent by weight. In some embodiments, the concentration is from about 0.0006 to 90 percent by weight. In compositions designed to be employed as concentrates, the active ingredients, in certain embodiments, are present in a concentration from about 0.1 to 98 weight percent, and in certain embodiment's about 0.5 to 90 weight percent. Such compositions are, in certain embodiments, diluted with an inert carrier, such as water, before application. The diluted compositions usually applied to weeds or the locus of weeds contain, in certain embodiments, about 0.0006 to 3.0 weight percent active ingredient and in certain embodiments contain about 0.01 to 1.0 weight percent.

The present compositions can be applied to weeds or their locus by the use of conventional ground or aerial dusters, sprayers, and granule applicators, by addition to irrigation or paddy water, and by other conventional means known to those skilled in the art.

The described embodiments and following examples are for illustrative purposes and are not intended to limit the scope of the claims. Other modifications, uses, or combinations with respect to the compositions described herein will be apparent to a person of ordinary skill in the art without departing from the spirit and scope of the claimed subject matter.

EXAMPLES

Results in Examples I, II, III, and IV are greenhouse trial results.

Example I

Evaluation of Postemergence Foliar-Applied Herbicidal Mixtures for Weed Control in Direct Seeded Rice Seeds or nutlets of the desired test plant species were planted in a soil matrix prepared by mixing a loam or sandy loam soil (e.g., 28.6 percent silt, 18.8 percent clay, and 52.6 percent sand, with a pH of about 5.8 and an organic matter content of about 1.8 percent) and calcareous grit in an 80 to 20 ratio. The soil matrix was contained in plastic pots with a volume of 1 quart and a surface area of 83.6 cm$^2$. When required to ensure good germination and healthy plants, a fungicide treatment and/or other chemical or physical treatment was applied. The plants were grown for 8-22 days in a greenhouse with an approximate 14 h photoperiod which was maintained at about 29° C. during the day and 26° C. during the night. Nutrients (Peters Excel® 15-5-15 5-Ca 2-Mg and iron chelate) were applied in the irrigation solution as needed and water was added on a regular basis. Supplemental lighting was provided with overhead metal halide 1000-Watt lamps as necessary. The plants were employed for testing when they reached the first through fourth true leaf stage.

Treatments consisted of the acid or esters of 4-amino-3-chloro-5-fluoro-6-(4-chloro-2-fluoro-3-methoxy-phenyl) pyridine-2-carboxylic acid (Compound A), each formulated as an SC (suspension concentrate), and various herbicidal components alone and in combination. Forms of compound A were applied on an acid equivalent basis.

Forms of compound A (compound of formula I) tested include:

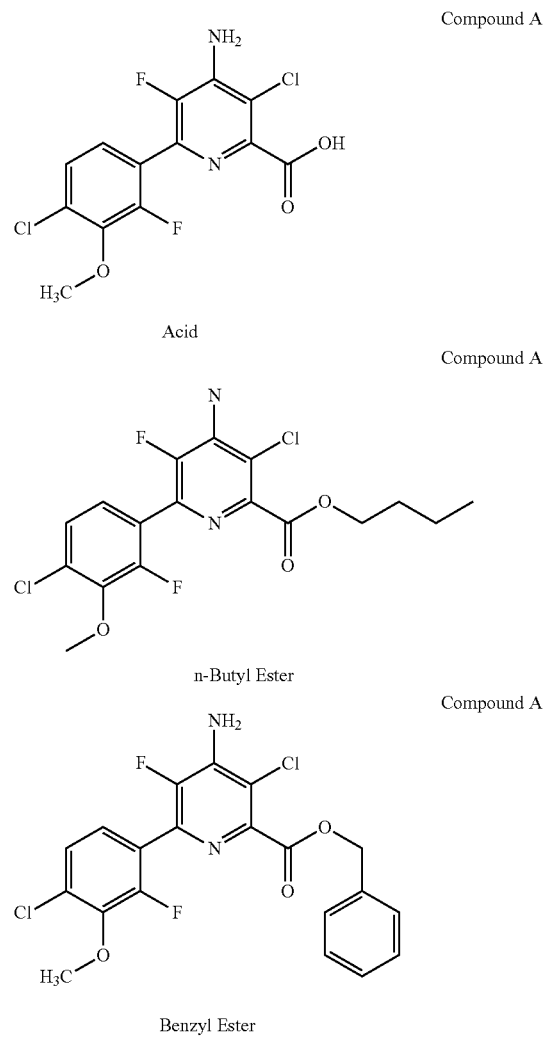

Other herbicidal components were applied on an acid equivalent basis and include acetolactate synthase (ALS)-inhibiting herbicides (imidazolinone chemical class) imazethapyr ammonium salt formulated as Newpath®, imazamox ammonium salt formulated as Beyond®, imazapic ammonium salt formulated as Plateau®, imazapyr isopropylamine salt formulated as Arsenal®, imazamethabenz-methyl (technical material) and imazaquin isopropylamine salt formulated as Scepter®/Imagine®.

Treatment requirements were calculated based upon the rates being tested, the concentration of active ingredient or acid equivalent in the formulation, and a 12 mL application volume at a rate of 187 L/ha.

For treatments comprised of formulated compounds, measured amounts of compounds were placed individually in 25 mL glass vials and diluted in a volume of 1.25% (v/v) Agri-Dex® crop oil concentrated to obtain 12× stock solutions. If a test compound did not dissolve readily, the mixture was warmed and/or sonicated. Application solutions were prepared by adding an appropriate amount of each stock solution (e.g., 1 mL) and diluted to the appropriate final concentrations with the addition of 10 mL of an aqueous mixture of 1.25%

(v/v) crop oil concentrate so that the final spray solutions contained 1.25+/−0.05% (v/v) crop oil concentrate.

For treatments comprised of technical compounds, weighed amounts can be placed individually in 25 mL glass vials and dissolved in a volume of 97:3 v/v acetone/DMSO to obtain 12× stock solutions. If a test compound does not dissolve readily, the mixture can be warmed and/or sonicated. Application solutions can be prepared by adding an appropriate amount of each stock solution (e.g., 1 mL) and diluted to the appropriate final concentrations with the addition of 10 mL of an aqueous mixture of 1.5% (v/v) crop oil concentrate so that the final spray solutions contain 1.25% (v/v) crop oil concentrate. When technical materials are used, the concentrated stock solutions can be added to the spray solutions so that the final acetone and DMSO concentrations of the application solutions are 16.2% and 0.5%, respectively.

For treatments comprised of formulated and technical compounds, weighed amounts of the technical materials were placed individually in 25 mL glass vials and dissolved in a volume of 97:3 v/v acetone/DMSO to obtain 12× stock solutions, and measured amounts of the formulated compounds were placed individually in 25 mL glass vials and diluted in a volume of 1.5% (v/v) crop oil concentrate or water to obtain 12× stock solutions. If a test compound did not dissolve readily, the mixture was warmed and/or sonicated. Application solutions were prepared by adding an appropriate amount of each stock solution (e.g., 1 mL) and diluted to the appropriate final concentrations with the addition of an appropriate amount of an aqueous mixture of 1.5% (v/v) crop oil concentrate so that the final spray solutions contained 1.25% (v/v) crop oil concentrate. As required, additional water and/or 97:3 v/v acetone/DMSO was added to individual application solutions so that the final acetone and DMSO concentrations of the application solutions being compared were 8.1% and 0.25%, respectively.

All stock solutions and applications solutions were visually inspected for compound compatibility prior to application. Spray solutions were applied to the plant material with an overhead Mandel track sprayer equipped with an 8002E nozzle calibrated to deliver 187 L/ha over an application area of 0.503 m$^2$ at a spray height of 18 to 20 inches (46 to 50 cm) above average plant canopy height. Control plants were sprayed in the same manner with the solvent blank.

The treated plants and control plants were placed in a greenhouse as described above and watered by sub-irrigation to prevent wash-off of the test compounds. After approximately 3 weeks, the condition of the test plants as compared with that of the untreated plants was determined visually and scored on a scale of 0 to 100 percent where 0 corresponds to no injury or growth inhibition and 100 corresponds to complete kill.

Colby's equation was used to determine the herbicidal effects expected from the mixtures (Colby, S. R. 1967. Calculation of the synergistic and antagonistic response of herbicide combinations. Weeds 15:20-22.).

The following equation was used to calculate the expected activity of mixtures containing two active ingredients, A and B:

$$\text{Expected} = A + B - (A \times B/100)$$

A=observed efficacy of active ingredient A at the same concentration as used in the mixture.

B=observed efficacy of active ingredient B at the same concentration as used in the mixture.

The compounds tested, application rates employed, plant species tested, and results are given in Tables 1-12

TABLE 1

Synergistic Activity of Foliar-Applied Compound A Acid and Imazethapyr Ammonium Herbicidal Compositions on Weed Control in a Rice Cropping System.

| Compound A Acid | Imazethapyr ammonium | Visual Weed Control (%) - 25 DAA LEFCH | |
|---|---|---|---|
| gae/ha | gae/ha | Obs | Exp |
| 8.75 | 0 | 10 | — |
| 17.5 | 0 | 45 | — |
| 0 | 8.75 | 20 | — |
| 8.75 | 8.75 | 60 | 28 |
| 17.5 | 8.75 | 95 | 56 |

TABLE 2

Synergistic Activity of Foliar-Applied Compound A Benzyl Ester and Imazethapyr Ammonium Herbicidal Compositions on Weed Control in a Rice Cropping System.

| Compound A Benzyl Ester | Imazethapyr ammonium | Visual Weed Control (%) - 25 DAA LEFCH | | Compound A Benzyl Ester | Imazethapyr ammonium | Visual Weed Control (%) - 25 DAA CYPES | |
|---|---|---|---|---|---|---|---|
| gae/ha | gae/ha | Obs | Exp | gae/ha | gae/ha | Obs | Exp |
| 8.75 | 0 | 70 | — | 4.38 | 0 | 70 | — |
| 17.5 | 0 | 70 | — | 17.5 | 0 | 85 | — |
| 0 | 8.75 | 20 | — | 0 | 8.75 | 0 | — |
| 8.75 | 8.75 | 90 | 76 | 4.38 | 8.75 | 90 | 70 |
| 17.5 | 8.75 | 90 | 76 | 17.5 | 8.75 | 100 | 85 |

TABLE 3

Synergistic Activity of Foliar-Applied Compound A n-Butyl Ester and Imazethapyr Ammonium Herbicidal Compositions on Weed Control in a Rice Cropping System.

| Compound An-Butyl Ester | Imazethapyr ammonium | Visual Weed Control (%) - 20 DAA DIGSA | |
|---|---|---|---|
| gae/ha | gae/ha | Obs | Exp |
| 16 | 0 | 15 | — |
| 0 | 70 | 80 | — |
| 16 | 70 | 90 | 83 |

TABLE 4

Synergistic Activity of Foliar-Applied Compound A Acid and Imazamox Ammonium Herbicidal Compositions on Weed Control in a Rice Cropping System.

| Compound A Acid | Imazamox ammonium | Visual Weed Control (%) - 25 DAA | | | |
|---|---|---|---|---|---|
| | | ECHCG | | CYPES | |
| gae/ha | gae/ha | Obs | Exp | Obs | Exp |
| 4.38 | 0 | 20 | — | 50 | — |
| 0 | 5.6 | 15 | — | 0 | — |
| 0 | 11.2 | 20 | — | 0 | — |
| 0 | 22.4 | 60 | — | 20 | — |
| 4.38 | 5.6 | 40 | 32 | 60 | 50 |
| 4.38 | 11.2 | 90 | 36 | 70 | 50 |
| 4.38 | 22.4 | 85 | 68 | 85 | 60 |

| Compound A Acid | Imazamox ammonium | Visual Weed Control (%) - 25 DAA LEFCH | |
|---|---|---|---|
| gae/ha | gae/ha | Obs | Exp |
| 4.38 | 0 | 0 | — |
| 8.75 | 0 | 10 | — |
| 0 | 11.2 | 20 | — |
| 4.38 | 11.2 | 40 | 20 |
| 8.75 | 11.2 | 70 | 28 |

| Compound A Acid | Imazamox ammonium | Visual Weed Control (%) - 20 DAA DIGSA | |
|---|---|---|---|
| gae/ha | gae/ha | Obs | Exp |
| 19.3 | 0 | 13 | — |
| 0 | 44.8 | 60 | — |
| 19.3 | 44.8 | 75 | 65 |

TABLE 5

Synergistic Activity of Foliar-Applied Compound A Benzyl Ester and Imazamox Ammonium Herbicidal Compositions on Weed Control in a Rice Cropping System.

| Compound A Benzyl Ester | Imazamox ammonium | Visual Weed Control (%) - 25 DAA | |
|---|---|---|---|
| gae/ha | gae/ha | Obs | Exp |
| | | CYPES | |
| 4.38 | 0 | 70 | — |
| 8.75 | 0 | 90 | — |
| 17.5 | 0 | 85 | — |
| 0 | 11.2 | 0 | — |
| 4.38 | 11.2 | 90 | 70 |
| 8.75 | 11.2 | 90 | 90 |
| 17.5 | 11.2 | 95 | 85 |
| | | CYPIR | |
| 8.75 | 0 | 75 | — |
| 0 | 11.2 | 20 | — |
| 0 | 22.4 | 70 | — |
| 8.75 | 11.2 | 100 | 80 |
| 8.75 | 22.4 | 95 | 93 |

TABLE 6

Synergistic Activity of Foliar-Applied Compound A Acid and Imazapic Ammonium Herbicidal Compositions on Control of Weeds Common to Rice Cropping Systems.

| Compound A Acid | Imazapic ammonium | Visual Weed Control (%) - 25 DAA ECHCG | |
|---|---|---|---|
| gae/ha | gae/ha | Obs | Exp |
| 4.38 | 0 | 20 | — |
| 8.75 | 0 | 50 | — |
| 0 | 4.38 | 20 | — |
| 0 | 8.75 | 40 | — |
| 4.38 | 4.38 | 60 | 36 |
| 8.75 | 4.38 | 75 | 60 |
| 4.38 | 8.75 | 75 | 52 |
| 8.75 | 8.75 | 75 | 70 |

| Compound A Acid | Imazapic ammonium | Visual Weed Control (%) - 25 DAA | | | |
|---|---|---|---|---|---|
| | | ECHCO | | LEFCH | |
| gae/ha | gae/ha | Obs | Exp | Obs | Exp |
| 4.38 | 0 | 60 | — | 0 | — |
| 8.75 | 0 | 65 | — | 10 | — |
| 17.5 | 0 | 90 | — | 45 | — |
| 0 | 17.5 | 70 | — | 50 | — |
| 4.38 | 17.5 | 99 | 88 | 65 | 50 |
| 8.75 | 17.5 | 100 | 90 | 60 | 55 |
| 17.5 | 17.5 | 100 | 97 | 75 | 73 |

| Compound A Acid | Imazapic ammonium | Visual Weed Control (%) - 20 DAA LEFCH | |
|---|---|---|---|
| gae/ha | gae/ha | Obs | Exp |
| 19.4 | 0 | 5 | — |
| 0 | 35 | 85 | — |
| 19.4 | 35 | 95 | 86 |

TABLE 7

Synergistic Activity of Foliar-Applied Compound A Benzyl Ester and Imazapic Ammonium Herbicidal Compositions on Control of Weeds Common to Rice Cropping Systems.

| Compound A Benzyl Ester | Imazapic ammonium | Visual Weed Control (%) - 22 DAA CYPIR | |
|---|---|---|---|
| gae/ha | gae/ha | Obs | Exp |
| 8 | 0 | 20 | — |
| 16 | 0 | 85 | — |
| 0 | 7 | 20 | — |
| 8 | 7 | 99 | 36 |
| 16 | 7 | 100 | 88 |

TABLE 8

Synergistic Activity of Foliar-Applied Compound A Acid and Imazapyr IPA (isopropylamine) Herbicidal Compositions on Control of Weeds Common to Rice Cropping Systems.

| Compound A Acid | Imazapyr IPA | Visual Weed Control (%) - 21 DAA IPOHE | |
|---|---|---|---|
| gae/ha | gae/ha | Obs | Exp |
| 4.38 | 0 | 0 | — |
| 8.75 | 0 | 10 | — |
| 17.5 | 0 | 30 | — |
| 0 | 4.38 | 50 | — |
| 0 | 8.75 | 40 | — |
| 4.38 | 4.38 | 85 | 50 |
| 8.75 | 4.38 | 85 | 55 |
| 17.5 | 4.38 | 90 | 65 |
| 4.38 | 8.75 | 90 | 40 |
| 8.75 | 8.75 | 90 | 46 |
| 17.5 | 8.75 | 85 | 58 |

TABLE 9

Synergistic Activity of Foliar-Applied Compound A Benzyl Ester and Imazapyr IPA (isopropylamine) Herbicidal Compositions on Control of Weeds Common to Rice Cropping Systems.

| Compound A Benzyl Ester | Imazapyr IPA | Visual Weed Control (%) - 21 DAA IPOHE | |
|---|---|---|---|
| gae/ha | gae/ha | Obs | Exp |
| 4.38 | 0 | 0 | — |
| 8.75 | 0 | 10 | — |
| 17.5 | 0 | 25 | — |
| 0 | 4.38 | 50 | — |
| 0 | 8.75 | 40 | — |
| 4.38 | 4.38 | 85 | 50 |
| 8.75 | 4.38 | 85 | 55 |
| 17.5 | 4.38 | 90 | 63 |
| 4.38 | 8.75 | 85 | 40 |
| 8.75 | 8.75 | 85 | 46 |
| 17.5 | 8.75 | 90 | 55 |

TABLE 10

Synergistic Activity of Foliar-Applied Compound A Acid and Imazaquin IPA (isopropylamine) Herbicidal Compositions on Control of Weeds Common to Rice Cropping Systems.

| Compound A Acid | Imazaquin IPA | Visual Weed Control (%) - 21 DAA IPOHE | |
|---|---|---|---|
| gae/ha | gae/ha | Obs | Exp |
| 4.38 | 0 | 0 | — |
| 8.75 | 0 | 10 | — |
| 17.5 | 0 | 30 | — |
| 0 | 9 | 0 | — |
| 4.38 | 9 | 15 | 0 |
| 8.75 | 9 | 15 | 10 |
| 17.5 | 9 | 50 | 30 |

TABLE 11

Synergistic Activity of Foliar-Applied Compound A Benzyl Ester and Imazaquin IPA (isopropylamine) Herbicidal Compositions on Control of Weeds Common to Rice Cropping Systems.

| Compound A Benzyl Ester | Imazaquin IPA | Visual Weed Control (%) - 21 DAA IPOHE | |
|---|---|---|---|
| gae/ha | gae/ha | Obs | Exp |
| 4.38 | 0 | 0 | — |
| 8.75 | 0 | 10 | — |
| 0 | 18 | 10 | — |
| 0 | 36 | 0 | — |
| 4.38 | 18 | 10 | 10 |
| 8.75 | 18 | 30 | 19 |
| 4.38 | 36 | 10 | 0 |
| 8.75 | 36 | 25 | 10 |

TABLE 12

Synergistic Activity of Foliar-Applied Compound A Benzyl Ester and Imazamethabenz-methyl Herbicidal Compositions on Control of Weeds Common to Rice Cropping Systems.

| Compound A Benzyl Ester | Imazamethabenz-methyl | Visual Weed Control (%) - 22 DAA CYPIR | |
|---|---|---|---|
| gae/ha | gai/ha | Obs | Exp |
| 8 | 0 | 30 | — |
| 0 | 43.75 | 0 | — |
| 0 | 87.5 | 20 | — |
| 0 | 175 | 25 | — |
| 8 | 43.75 | 65 | 30 |
| 8 | 87.5 | 65 | 44 |
| 8 | 175 | 65 | 48 |

| | | |
|---|---|---|
| CYPES | *Cyperus esculentus* L. | nutsedge, yellow |
| CYPIR | *Cyperus iria* L. | flatsedge, rice |
| DIGSA | *Digitaria sanguinalis* (L.) Scop. | crabgrass, large |
| ECHCG | *Echinochloa crusgalli* (L.) Beauv. | barnyardgrass |
| ECHCO | *Echinochloa colona* (L.) Link | junglerice |
| IPOHE | *Ipomoea hederacea* Jacq. | morningglory, ivyleaf |
| LEFCH | *Leptochloa chinensis* (L.) Nees | sprangletop, Chinese | gae/ha = grams acid equivalent per hectare
gai/ha = grams active ingredient per hectare
Obs = observed value
Exp = expected value as calculated by Colby's equation
DAA = days after application Example II Evaluation of in-Water Applied Herbicidal Mixtures for Weed Control in Transplanted Paddy Rice Weed seeds or nutlets of the desired test plant species were planted in puddled soil (mud) prepared by mixing a shredded, non-sterilized mineral soil (50.5 percent silt, 25.5 percent clay, and 24 percent sand, with a pH of about 7.6 and an organic matter content of about 2.9 percent) and water at a 1:1 volumetric ratio. The prepared mud was dispensed in 365 mL aliquots into 16-ounce (oz.) non-perforated plastic pots with a surface area of 86.59 square centimeters ($cm^2$) leaving a headspace of 3 centimeters (cm) in each pot. Mud was allowed to dry overnight prior to planting or transplanting. Rice seeds were planted in Sun Gro MetroMix® 306 planting mixture, which typically has a pH of about 6.0 to about 6.8 and an organic matter content of about 30 percent, in plastic plug trays. Seedlings at the second or third leaf stage of growth were transplanted into 860 mL of mud contained in 32-oz. non-perforated plastic pots with a surface area of 86.59 cm$^2$ 4 days prior to herbicide application. The paddy was created by filling the headspace of the pots with 2.5 to 3 cm of water. When required to ensure good germination and healthy plants, a fungicide treatment and/or other chemical or physical treatment was applied. The plants were grown for 4-22 days in a greenhouse with an approximate 14 h photoperiod which was maintained at about 29° C. during the day and about 26° C. during the night. Nutrients were added as Osmocote® (19:6:12, N:P:K+minor nutrients) at 2 g per 16-oz. pot and 4 g per 32-oz. pot. Water was added on a regular basis to maintain the paddy flood, and supplemental lighting was provided with overhead metal halide 1000-Watt lamps as necessary. The plants were employed for testing when they reached the first through fourth true leaf stage.

Treatments consisted of the acid or esters of 4-amino-3-chloro-5-fluoro-6-(4-chloro-2-fluoro-3-methoxy-phenyl)pyridine-2-carboxylic acid (compound A) each formulated as an SC and various herbicidal components alone and in combination. Forms of compound A were applied on an acid equivalent basis.

Forms of compound A (compound of formula I) tested include:

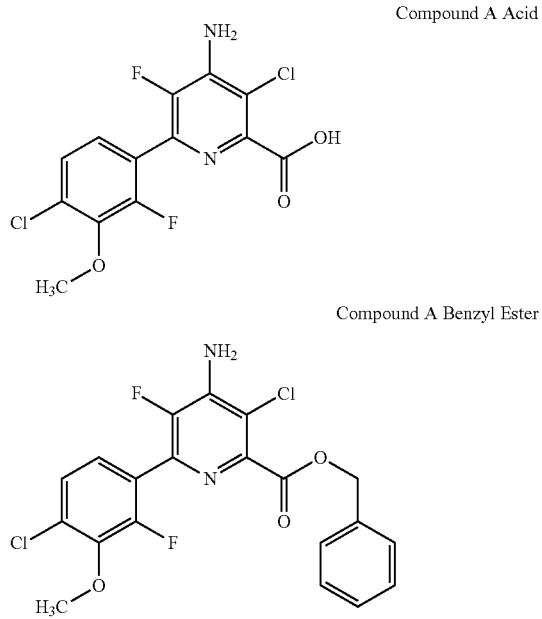 [SMILES: COc1c(Cl)ccc(-c2nc(C(=O)O)c(Cl)c(N)c2F)c1F ; COc1c(Cl)ccc(-c2nc(C(=O)OCc3ccccc3)c(Cl)c(N)c2F)c1F]

Compound A Acid

Compound A Benzyl Ester

Other herbicidal components were applied on an acid equivalent basis and included the acetolactate synthase (ALS)-inhibiting imidazolinone herbicides imazethapyr ammonium salt formulated as Newpath®, imazamox ammonium salt formulated as Beyond®, imazapic ammonium salt formulated as Plateau®, imazapyr isopropylamine salt formulated as Arsenal®, imazamethabenz-methyl (technical material), and imazaquin isopropylamine salt formulated as Scepter®.

Treatment requirements for each compound or herbicidal component were calculated based upon the rates being tested, the concentration of active ingredient or acid equivalent in the formulation, an application volume of 2 mL per component per pot, and an application area of 86.59 cm$^2$ per pot.

For formulated compounds, a measured amount was placed in an individual 100 or 200 mL glass vial and was dissolved in a volume of 1.25% (v/v) Agri-Dex® crop oil concentrate to obtain application solutions. If the test compound did not dissolve readily, the mixture was warmed and/or sonicated.

For technical grade compounds, a weighed amount was placed in an individual 100 to 200 mL glass vial and was dissolved in a volume of acetone to obtain concentrated stock solutions. If the test compound did not dissolve readily, the mixture was warmed and/or sonicated. The concentrated stock solutions obtained were diluted with an equivalent volume of an aqueous mixture containing 2.5% (v/v) crop oil concentrate so that the final application solutions contained 1.25% (v/v) crop oil concentrate.

Applications were made by injecting with a pipetter appropriate amounts of the application solutions, individually and sequentially, into the aqueous layer of the paddy. Control plants were treated in the same manner with the solvent blank. Applications were made so that all treated plant material received the same concentrations of acetone and crop oil concentrate.

The treated plants and control plants were placed in a greenhouse as described above and water was added as needed to maintain a paddy flood. After approximately 3 weeks the condition of the test plants as compared with that of the untreated plants was determined visually and scored on a scale of 0 to 100 percent where 0 corresponds to no injury or growth inhibition and 100 corresponds to complete kill.

Colby's equation was used to determine the herbicidal effects expected from the mixtures (Colby, S. R. 1967. Calculation of the synergistic and antagonistic response of herbicide combinations. Weeds 15:20-22.).

The following equation was used to calculate the expected activity of mixtures containing two active ingredients, A and B:

Expected=$A+B-(A\times B/100)$

A=observed efficacy of active ingredient A at the same concentration as used in the mixture.

B=observed efficacy of active ingredient B at the same concentration as used in the mixture.

Some of the compounds tested, application rates employed, plant species tested, and results are given in Tables 13-20.

TABLE 13

Synergistic Activity of In-Water Applications of Compound A Acid and Imazethapyr Ammonium Herbicidal Compositions on Weed Control in a Rice Cropping System.

| Compound A Acid | Imazethapyr ammonium | Visual Weed Control (%) - 25 DAA ECHCG | | Compound A Acid | Imazethapyr ammonium | Visual Weed Control (%) - 25 DAA ECHOR | |
|---|---|---|---|---|---|---|---|
| gae/ha | gae/ha | Obs | Exp | gae/ha | gae/ha | Obs | Exp |
| 17.5 | 0 | 0 | — | 8.75 | 0 | 0 | — |
| 35 | 0 | 0 | — | 17.5 | 0 | 0 | — |

TABLE 13-continued

Synergistic Activity of In-Water Applications of Compound A Acid and Imazethapyr Ammonium Herbicidal Compositions on Weed Control in a Rice Cropping System.

| Compound A Acid | Imazethapyr ammonium | Visual Weed Control (%) - 25 DAA ECHCG | | Compound A Acid | Imazethapyr ammonium | Visual Weed Control (%) - 25 DAA ECHOR | |
|---|---|---|---|---|---|---|---|
| gae/ha | gae/ha | Obs | Exp | gae/ha | gae/ha | Obs | Exp |
| 0 | 17.5 | 0 | — | 0 | 17.5 | 0 | — |
| 17.5 | 17.5 | 20 | 0 | 8.75 | 17.5 | 15 | 0 |
| 35 | 17.5 | 20 | 0 | 17.5 | 17.5 | 25 | 0 |

TABLE 14

Synergistic Activity of In-Water Applications of Compound A Benzyl Ester and Imazethapyr Ammonium Herbicidal Compositions on Weed Control in a Rice Cropping System.

| Compound A Benzyl Ester | Imazethapyr ammonium | Visual Weed Control (%) - 25 DAA ECHCG | |
|---|---|---|---|
| gae/ha | gae/ha | Obs | Exp |
| 17.5 | 0 | 10 | — |
| 0 | 8.75 | 0 | — |
| 0 | 17.5 | 0 | — |
| 0 | 35 | 50 | — |
| 17.5 | 8.75 | 30 | 10 |
| 17.5 | 17.5 | 70 | 10 |
| 17.5 | 35 | 60 | 55 |

| Compound A Benzyl Ester | Imazethapyr ammonium | Visual Weed Control (%) - 25 DAA ECHOR | | LEFCH | |
|---|---|---|---|---|---|
| gae/ha | gae/ha | Obs | Exp | Obs | Exp |
| 8.75 | 0 | 0 | — | 0 | — |
| 0 | 8.75 | 0 | — | 0 | — |
| 0 | 17.5 | 0 | — | 0 | — |
| 0 | 35 | 25 | — | 95 | — |
| 8.75 | 8.75 | 15 | 0 | 80 | 0 |
| 8.75 | 17.5 | 10 | 0 | 55 | 0 |
| 8.75 | 35 | 45 | 25 | 90 | 95 |

TABLE 15

Synergistic Activity of In-Water Applications of Compound A Acid and Imazamox Ammonium Herbicidal Compositions on Weed Control in a Rice Cropping System.

| Compound A Acid | Imazamox ammonium | Visual Weed Control (%) - 25 DAA ECHOR | |
|---|---|---|---|
| gae/ha | gae/ha | Obs | Exp |
| 8.75 | 0 | 0 | — |
| 17.5 | 0 | 0 | — |
| 35 | 0 | 10 | — |
| 0 | 11.2 | 0 | — |
| 8.75 | 11.2 | 0 | 0 |
| 17.5 | 11.2 | 20 | 0 |
| 35 | 11.2 | 25 | 10 |

TABLE 16

Synergistic Activity of In-Water Applications of Compound A Benzyl Ester and Imazamox Ammonium Herbicidal Compositions on Weed Control in a Rice Cropping System.

| Compound A Benzyl Ester | Imazamox ammonium | Visual Weed Control (%) - 25 DAA ECHCG | | Compound A Benzyl Ester | Imazamox ammonium | Visual Weed Control (%) - 25 DAA ECHOR | |
|---|---|---|---|---|---|---|---|
| gae/ha | gae/ha | Obs | Exp | gae/ha | gae/ha | Obs | Exp |
| 17.5 | 0 | 10 | — | 8.75 | 0 | 0 | — |
| 35 | 0 | 45 | — | 0 | 5.6 | 0 | — |
| 0 | 5.6 | 0 | — | 0 | 11.2 | 0 | — |
| 0 | 22.4 | 25 | — | 0 | 22.4 | 0 | — |
| 17.5 | 5.6 | 35 | 10 | 8.75 | 5.6 | 15 | 0 |
| 35 | 5.6 | 50 | 45 | 8.75 | 11.2 | 15 | 0 |
| 17.5 | 22.4 | 55 | 33 | 8.75 | 22.4 | 25 | 0 |
| 35 | 22.4 | 85 | 59 | | | | |

TABLE 17

Synergistic Activity of In-Water Applications of Compound A Acid and Imazapic Ammonium Herbicidal Compositions on Control of Weeds Common to Rice Cropping Systems.

| Compound A Acid | Imazapic ammonium | Visual Weed Control (%) - 25 DAA | | | |
|---|---|---|---|---|---|
| | | ECHCG | | CHOR | |
| gae/ha | gae/ha | Obs | Exp | Obs | Exp |
| 8.75 | 0 | 0 | — | 0 | — |
| 17.5 | 0 | 0 | — | 0 | — |
| 35 | 0 | 0 | — | 10 | — |
| 0 | 17.5 | 20 | — | 0 | — |
| 8.75 | 17.5 | 25 | 20 | 15 | 0 |
| 17.5 | 17.5 | 40 | 20 | 20 | 0 |
| 35 | 17.5 | 50 | 20 | 35 | 10 |

| Compound A Acid | Imazapic ammonium | Visual Weed Control (%) - 19 DAA ECHOR | |
|---|---|---|---|
| gae/ha | gae/ha | Obs | Exp |
| 42 | 0 | 15 | — |
| 0 | 35 | 78 | — |
| 42 | 35 | 95 | 81 |

TABLE 18

Synergistic Activity of In-Water Applications of Compound A Benzyl Ester and Imazapic Ammonium Herbicidal Compositions on Control of Weeds Common to Rice Cropping Systems.

| Compound A Benzyl Ester | Imazapic ammonium | Visual Weed Control (%) - 25 DAA ECHCG | | Compound A Benzyl Ester | Imazapic ammonium | Visual Weed Control (%) - 25 DAA ECHOR | |
|---|---|---|---|---|---|---|---|
| gae/ha | gae/ha | Obs | Exp | gae/ha | gae/ha | Obs | Exp |
| 35 | 0 | 45 | — | 8.75 | 0 | 0 | — |
| 0 | 8.75 | 20 | — | 0 | 4.38 | 0 | — |
| 0 | 17.5 | 20 | — | 0 | 8.75 | 0 | — |
| 35 | 8.75 | 95 | 56 | 0 | 17.5 | 0 | — |
| 35 | 17.5 | 95 | 56 | 8.75 | 4.38 | 10 | 0 |
| | | | | 8.75 | 8.75 | 15 | 0 |
| | | | | 8.75 | 17.5 | 30 | 0 |

TABLE 19

Synergistic Activity of In-Water Applications of Compound A Acid and Imazapyr IPA (isopropylamine) Herbicidal Compositions on Control of Weeds Common to Rice Cropping Systems.

| Compound A Acid gae/ha | Imazapyr IPA gae/ha | Obs | Exp |
|---|---|---|---|
| | | Visual Weed Control (%) - 22 DAA ECHOR | |
| 10.6 | 0 | 15 | — |
| 42.4 | 0 | 40 | — |
| 0 | 70 | 50 | — |
| 0 | 140 | 85 | — |
| 10.6 | 70 | 45 | 58 |
| 42.4 | 70 | 85 | 70 |
| 10.6 | 140 | 99 | 87 |
| 42.4 | 140 | 100 | 91 |
| | | Visual Weed Control (%) - 22 DAA CYPRO | |
| 10.6 | 0 | 0 | — |
| 21.2 | 0 | 40 | — |
| 0 | 70 | 70 | — |
| 10.6 | 70 | 85 | 70 |
| 21.2 | 70 | 90 | 82 |

TABLE 20

Synergistic Activity of In-Water Applications of Compound A Benzyl Ester and Imazapyr IPA (isopropylamine) Herbicidal Compositions on Control of Weeds Common to Rice Cropping Systems.

| Compound A Benzyl Ester | Imazapyr IPA | Visual Weed Control (%) - 22 DAA ECHOR | |
|---|---|---|---|
| gae/ha | gae/ha | Obs | Exp |
| 17.5 | 0 | 30 | — |
| 0 | 70 | 50 | — |
| 0 | 140 | 85 | — |
| 17.5 | 70 | 90 | 65 |
| 17.5 | 140 | 99 | 90 |

| | | |
|---|---|---|
| CYPRO | *Cyperus rotundus* L. | nutsedge, purple |
| ECHCG | *Echinochloa crusgalli* (L.) Beauv. | barnyardgrass |
| ECHOR | *Echinochloa oryzoides* (Ard.) Fritsch | watergrass, early |
| LEFCH | *Leptochloa chinensis* (L.) Nees | sprangletop, Chinese | gae/ha = grams acid equivalent per hectare
gai/ha = grams active ingredient per hectare
Obs = observed value
Exp = expected value as calculated by Colby's equation
DAA = days after application

Example III

Evaluation of Postemergence Foliar-Applied Herbicidal Mixtures for General Weed Control

Seeds or nutlets of the desired test plant species were planted in Sun Gro Metro-Mix® 360 planting mixture, which typically has a pH of about 6.0 to about 6.8 and an organic matter content of about 30 percent, in plastic pots with a surface area of 84.6 cm² and a volume of 560 cubic centimeters (cm³). When required to ensure good germination and healthy plants, a fungicide treatment and/or other chemical or physical treatment was applied. The plants were grown for 7-31 days (d) in a greenhouse with an approximate 15 hour (h) photoperiod which was maintained at about 23-29° C. during the day and about 22-28° C. during the night. Nutrients (Peters Excel® 15-5-15 5-Ca 2-Mg) and water were added on a regular basis and supplemental lighting was provided with overhead metal halide 1000-Watt lamps as necessary. The plants were employed for testing when they reached the first, second, or third true leaf stage.

Treatment requirements were calculated based upon the rates being tested, the concentration of active ingredient or acid equivalent in the formulation, and a 12 mL application volume at a rate of 187 L/ha.

Treatments consisted of the acid or esters of 4-amino-3-chloro-5-fluoro-6-(4-chloro-2-fluoro-3-methoxy-phenyl) pyridine-2-carboxylic acid (Compound A), each formulated as an SC, and various herbicidal components alone and in combination. Forms of compound A were applied on an acid equivalent basis.

Forms of compound A (compound of formula I) tested include:

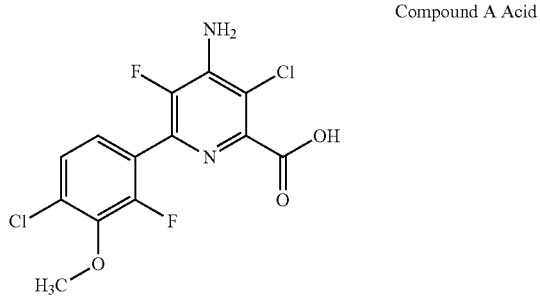 [SMILES: COc1c(Cl)ccc(-c2nc(C(=O)O)c(Cl)c(N)c2F)c1F]

Compound A Acid

Compound A Benzyl Ester

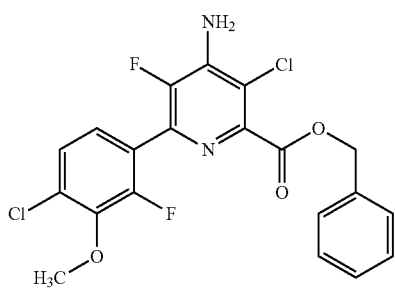

Other herbicidal components were applied on an acid equivalent basis and included acetolactate synthase (ALS)-inhibiting herbicides (imidazolinone chemical class) imazethapyr ammonium salt formulated as Newpath®, and imazapic ammonium salt formulated as Plateau®.

For treatments comprised of formulated compounds, measured amounts of compounds were placed individually in 25 mL glass vials and diluted in a volume of 1.25% (v/v) Agri-Dex® crop oil concentrated to obtain 12× stock solutions. If a test compound did not dissolve readily, the mixture was warmed and/or sonicated. Application solutions were prepared by adding an appropriate amount of each stock solution (typically 1 mL) and diluted to the appropriate final concentrations with the addition of 10 mL of an aqueous mixture of 1.25% (v/v) crop oil concentrate so that the final spray solutions contained 1.25+/−0.05% (v/v) crop oil concentrate.

For treatments comprised of technical compounds, weighed amounts can be placed individually in 25 mL glass vials and dissolved in a volume of 97:3 v/v acetone/DMSO to obtain 12× stock solutions. If a test compound does not dissolve readily, the mixture can be warmed and/or sonicated. Application solutions can be prepared by adding an appropriate amount of each stock solution (e.g., 1 mL) and diluted to the appropriate final concentrations with the addition of 10 mL of an aqueous mixture of 1.5% (v/v) crop oil concentrate so that the final spray solutions contain 1.25% (v/v) crop oil concentrate. When technical materials are used, the concentrated stock solutions can be added to the spray solutions so that the final acetone and DMSO concentrations of the application solutions are 16.2% and 0.5%, respectively.

For treatments comprised of formulated and technical compounds, weighed amounts of the technical materials can be placed individually in 25 mL glass vials and dissolved in a volume of 97:3 v/v acetone/DMSO to obtain 12× stock solutions, and measured amounts of the formulated compounds can be placed individually in 25 mL glass vials and diluted in a volume of 1.5% (v/v) crop oil concentrate or water to obtain 12× stock solutions. If a test compound does not dissolve readily, the mixture can be warmed and/or sonicated. Application solutions can be prepared by adding an appropriate amount of each stock solution (e.g., 1 mL) and diluted to the appropriate final concentrations with the addition of an appropriate amount of an aqueous mixture of 1.5% (v/v) crop oil concentrate so that the final spray solutions contain 1.25% (v/v) crop oil concentrate. As required, additional water and/or 97:3 v/v acetone/DMSO can be added to individual application solutions so that the final acetone and DMSO concentrations of the application solutions being compared are 8.1% and 0.25%, respectively.

All stock solutions and applications solutions were visually inspected for compound compatibility prior to application. Compound requirements are based upon a 12 mL application volume at a rate of 187 liters per hectare (L/ha). Formulated compounds were applied to the plant material with an overhead Mandel track sprayer equipped with an 8002E nozzle calibrated to deliver 187 L/ha over an application area of 0.503 square meters ($m^2$) at a spray height of 18 to 20 inches (46 to 50 cm) above the average plant canopy height. Control plants were sprayed in the same manner with the solvent blank.

The treated plants and control plants were placed in a greenhouse as described above and watered by sub-irrigation to prevent wash-off of the test compounds. After approximately 3 weeks, the condition of the test plants as compared with that of the untreated plants was determined visually and scored on a scale of 0 to 100 percent where 0 corresponds to no injury or growth inhibition and 100 corresponds to complete kill.

Colby's equation was used to determine the herbicidal effects expected from the mixtures (Colby, S. R. 1967. Calculation of the synergistic and antagonistic response of herbicide combinations. Weeds 15:20-22.).

The following equation was used to calculate the expected activity of mixtures containing two active ingredients, A and B:

$$\text{Expected} = A + B - (A \times B / 100)$$

A=observed efficacy of active ingredient A at the same concentration as used in the mixture.

B=observed efficacy of active ingredient B at the same concentration as used in the mixture.

Some of the compounds tested, application rates employed, plant species tested, and results are given in Tables 21-23.

TABLE 21

Synergistic Activity of Foliar-Applied Compound A Acid and Imazethapyr Ammonium Herbicidal Compositions for Weed Control.

| Compound A Acid | Imazethapyr ammonium | Visual Weed Control (%) - 19 DAA AVEFA | |
|---|---|---|---|
| gae/ha | gae/ha | Obs | Exp |
| 29 | 0 | 10 | — |
| 0 | 70 | 80 | — |
| 29 | 70 | 100 | 82 |

TABLE 22

Synergistic Activity of Foliar-Applied Compound A Acid and Imazapic Ammonium Herbicidal Compositions for Weed Control.

| Compound A Acid | Imazapic ammonium | Visual Weed Control (%) - 19 DAA | | | |
|---|---|---|---|---|---|
| | | ALOMY | | AVEFA | |
| gae/ha | gae/ha | Obs | Exp | Obs | Exp |
| 29 | 0 | 10 | — | 10 | — |
| 0 | 35 | 30 | — | 70 | — |
| 29 | 35 | 60 | 37 | 95 | 73 |

TABLE 23

Synergistic Activity of Foliar-Applied Compound A Benzyl Ester and Imazapic ammonium Herbicidal Compositions for Weed Control.

| Compound A Benzyl Ester | Imazapic ammonium | Visual Control (%) - 19 DAA ALOMY | |
|---|---|---|---|
| gae/ha | gae/ha | Obs | Exp |
| 24 | 0 | 20 | — |
| 0 | 35 | 30 | — |
| 24 | 35 | 100 | 44 |

ALOMY  *Alopecurus myosuroides* Huds.,  blackgrass
AVEFA  *Avena fatua* L.,  oat, wild
gae/ha = grams acid equivalent per hectare
gai/ha = grams active ingredient per hectare
Obs = observed value
Exp = expected value as calculated by Colby's equation
DAA = days after application Example IV Evaluation of Postemergence Herbicidal Activity of Mixtures in Forage Crops Seeds or root cuttings of the desired test plant species were planted in Sun Gro MetroMix® 306 planting mixture, which typically has a pH of about 6.0 to about 6.8 and an organic matter content of about 30 percent, in plastic pots with a surface area of 126.6 square centimeters ($cm^2$). When required to ensure good germination and healthy plants, a fungicide treatment and/or other chemical or physical treatment was applied. The plants were grown for 14-60 days in a greenhouse with an approximate 14 hour photoperiod which was maintained at about 28° C. during the day and about 24° C. during the night. Nutrients and water were added on a regular basis and supplemental lighting was provided with overhead metal halide 1000-Watt lamps as necessary. The plants were employed for testing when they reached the BBCH13 to BBCH23 leaf stage.

Treatments consisted of the benzyl ester of 4-amino-3-chloro-5-fluoro-6-(4-chloro-2-fluoro-3-methoxy-phenyl)pyridine-2-carboxylic acid (Compound A), formulated as a SC (suspension concentrate), and a second herbicide alone and in combination.
Forms of compound A (compound of formula I) tested include:

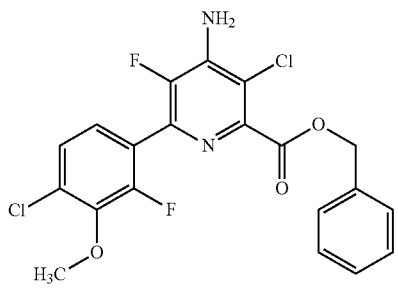
Compound A Benzyl Ester

A measured aliquot of Compound A was placed in a 25 milliliter (mL) glass vial and diluted in a volume of 1.25% (v/v) Agri-Dex® crop oil concentrate to obtain stock solutions. Compound requirements are based upon a 12 mL application volume at a rate of 187 liters per hectare (L/ha). Spray solutions of the second cereal herbicide and experimental compound mixtures were prepared by adding the stock solutions to the appropriate amount of dilution solution to form 12 mL spray solution with active ingredients in two- and three-way combinations. Formulated compounds were applied to the plant material with an overhead Mandel track sprayer equipped with an 8002E nozzle calibrated to deliver 187 L/ha over an application area of 0.503 square meters ($m^2$) at a spray height of 18 inches (46 cm) above average plant canopy. Control plants were sprayed in the same manner with the solvent blank.

The treated plants and control plants were placed in a greenhouse as described above and watered by sub-irrigation to prevent wash-off of the test compounds. After approximately 21 days, the condition of the test plants, as compared with that of the control plants, was determined visually and scored on a scale of 0 to 100 percent where 0 corresponds to no injury and 100 corresponds to complete kill.

Colby's equation was used to determine the herbicidal effects expected from the mixtures (Colby, S. R. 1967. Calculation of the synergistic and antagonistic response of herbicide combinations. Weeds 15:20-22.).

The following equation was used to calculate the expected activity of mixtures containing two active ingredients, A and B:

Expected=$A+B-(A\times B/100)$

A=observed efficacy of active ingredient A at the same concentration as used in the mixture.

B=observed efficacy of active ingredient B at the same concentration as used in the mixture.

Some of the compounds tested, application rates employed, plant species tested, and results are given in Table 24.

TABLE 24

Synergistic Activity of Foliar-Applied Compound A Benzyl Ester and Plateau Herbicide (Imazapic Ammonium) Herbicidal Compositions on Weed Control in a Forage System.

| Application Rate (gae/ha) | | CENMA | | SONAR | |
|---|---|---|---|---|---|
| Compound A Benzyl Ester | Imazapic ammonium | Obs | Exp | Obs | Exp |
| 4.4 | 0 | 70 | — | 65 | — |
| 8.8 | 0 | 85 | — | 100 | — |
| 17.5 | 0 | 95 | — | 95 | — |
| 0 | 8.75 | 0 | — | — | — |
| 0 | 17.5 | 0 | — | 0 | — |
| 4.4 | 8.75 | 98 | 70 | — | — |
| 8.8 | 8.75 | 100 | 85 | — | — |
| 17.5 | 8.75 | 100 | 95 | — | — |
| 4.4 | 17.5 | 95 | 70 | 90 | 65 |
| 8.8 | 17.5 | 95 | 85 | 90 | 100 |
| 17.5 | 17.5 | 100 | 95 | 95 | 95 |

CENMA  *Centaurea biebersteinii* DC.  knapweed, spotted
SONAR  *Sonchus arvensis* L.  sowthistle, perennial
gae/ha = grams acid equivalent per hectare
gai/ha = grams active ingredient per hectare
Obs = observed value
Exp = expected value as calculated by Colby's equation
DAA = days after application

Example V

Evaluation of Postemergence Herbicidal Activity of Mixtures in Cereal Crops in the Greenhouse Seeds of the desired test plant species were planted in Sun Gro MetroMix® 306 planting mixture, which typically has a pH of 6.0 to 6.8 and an organic matter content of about 30 percent, in plastic pots with a surface area of 103.2 square centimeters ($cm^2$). When required to ensure good germination and healthy plants, a fungicide treatment and/or other chemical or physical treatment was applied. The plants were grown for 7-36 days in a greenhouse with an approximate 14 hour photoperiod which was maintained at about 18° C. during the day and about 17° C. during the night. Nutrients and water were added on a regular basis and supplemental lighting was provided with overhead metal halide 1000-Watt lamps as necessary. The plants were employed for testing when they reached the second or third true leaf stage.

Treatments consisted of the benzyl ester of 4-amino-3-chloro-5-fluoro-6-(4-chloro-2-fluoro-3-methoxy-phenyl)pyridine-2-carboxylic acid (Compound A), formulated as an SC, a second cereal herbicide alone and then both in combination.

Forms of compound A (compound of formula I) tested include:

Compound A Benzyl Ester

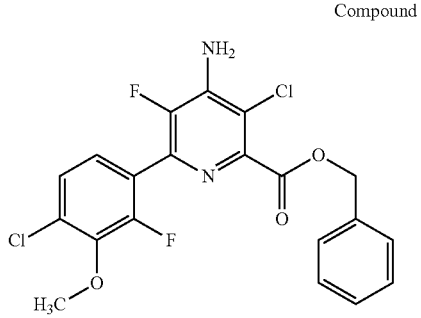

Other herbicidal components were applied on an acid equivalent basis and include acetolactate synthase (ALS)-inhibiting herbicides (imidazolinone chemical class) imazamethabenz-methyl formulated as Assert®. Spray solutions of the second cereal herbicide and experimental compound mixtures were prepared by adding the stock solutions to the appropriate amount of dilution solution to form 12 mL spray solution with active ingredients in two- and three-way combinations. Formulated compounds were applied to the plant material with an overhead Mandel track sprayer equipped with an 8002E nozzle calibrated to deliver 187 L/ha over an application area of 0.503 square meters ($m^2$) at a spray height of 18 inches (46 cm) above average plant canopy. Control plants were sprayed in the same manner with the solvent blank.

The treated plants and control plants were placed in a greenhouse as described above and watered by sub-irrigation to prevent wash-off of the test compounds. After 20-22 days, the condition of the test plants as compared with that of the control plants was determined visually and scored on a scale of 0 to 100 percent where 0 corresponds to no injury and 100 corresponds to complete kill.

Colby's equation was used to determine the herbicidal effects expected from the mixtures (Colby, S. R. 1967. Calculation of the synergistic and antagonistic response of herbicide combinations. Weeds 15:20-22.).

The following equation was used to calculate the expected activity of mixtures containing two active ingredients, A and B:

$$\text{Expected} = A + B - (A \times B/100)$$

A=observed efficacy of active ingredient A at the same concentration as used in the mixture.

B=observed efficacy of active ingredient B at the same concentration as used in the mixture.

The compounds tested, application rates employed, plant species tested, and results are given in Tables 25-26.

TABLE 25

Synergistic Activity of Foliar-Applied Compound A Benzyl Ester and Imazamethabenz-methyl Herbicidal Compositions on Weed Control in a Cereal Cropping System.

| Compound A Benzyl Ester | Imazamethabenz-methyl | Visual Weed Control (%) - 21 DAA | | | | | |
|---|---|---|---|---|---|---|---|
| | | CHEAL | | CIRAR | | PAPRH | |
| gae/ha | gai/ha | Obs | Exp | Obs | Exp | Obs | Exp |
| 2 | 0 | 50 | — | 10 | — | 20 | — |
| 4 | 0 | 60 | — | 20 | — | 70 | — |
| 0 | 200 | 0 | — | 0 | — | 0 | — |
| 2 | 200 | 60 | 50 | 30 | 10 | 60 | 20 |
| 4 | 200 | 85 | 60 | 40 | 20 | 90 | 70 |

TABLE 26

Synergistic Activity of Foliar-Applied Compound A Benzyl Ester and Imazamethabenz-methyl Herbicidal Compositions on Weed Control in a Cereal Cropping System.

| Compound A Benzyl Ester | Imazamethabenz-methyl | Visual Weed Control (%) - 21 DAA | | | | | |
|---|---|---|---|---|---|---|---|
| | | SASKR | | SINAR | | VERPE | |
| gae/ha | gai/ha | Obs | Exp | Obs | Exp | Obs | Exp |
| 2 | 0 | 10 | — | 60 | — | 0 | — |
| 4 | 0 | 60 | — | 70 | — | 5 | — |
| 0 | 200 | 70 | — | 70 | — | 0 | — |
| 2 | 200 | 85 | 73 | 95 | 88 | 0 | 0 |
| 4 | 200 | 85 | 88 | 95 | 91 | 30 | 5 |

| | | |
|---|---|---|
| CHEAL | *Chenopodium album* L. | lambsquarter, common |
| CIRAR | *Cirsium arvense* (L.) Scop. | thistle, Canada |
| PAPRH | *Papaver rhoeas* L. | poppy, common |
| SASKR | *Salsola iberica* L. | thistle, Russian |
| SINAR | *Sinapis arvensis* L. | mustard, wild |
| VERPE | *Veronica persica* Poir. | speedwell, bird's-eye |

What is claimed is:

1. A herbicidal composition comprising a herbicidally effective amount of (a) a compound of the formula (I):

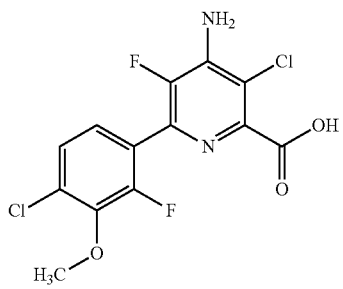

(I)

or a $C_{1-4}$ alkyl ester, or a benzyl ester, or an agriculturally acceptable salt of formula (I); and
(b) an imidazolinone herbicide, wherein (a) and (b) are present in the composition in a ratio such that the composition exhibits synergy.

2. The composition of claim 1, wherein (a) is a benzyl ester of the compound of formula (I).

3. The composition of claim 1, wherein (a) is the carboxylic acid of formula (I).

4. The composition of claim 1, wherein (b) is at least one compound or an agriculturally acceptable salt, carboxylic acid, carboxylate salt, or ester thereof, selected from the group consisting of imazethapyr, imazethapyr ammonium, imazamox, imazamox ammonium, imazapic, imazapic ammonium, imazapyr, imazapyr isopropylamine salt, imazamethabenz, imazamethabenz-methyl, imazaquin, and imazaquin isopropylamine salt.

5. The composition of claim 1, further comprising a herbicide safener, adjuvant and/or carrier.

6. The composition of claim 4, wherein the weight ratio of compound of formula (I) or agriculturally acceptable salt or ester thereof to imazethapyr or agriculturally acceptable salt or ester thereof is from about 4:1 to about 1:8.

7. The composition of claim 4, wherein the weight ratio of the compound of formula (I) or agriculturally acceptable salt or ester thereof to imazamox or agriculturally acceptable salt or ester thereof is from about 6:1 to about 1:1.

8. The composition of claim 4, wherein the weight ratio of the compound of formula (I) or agriculturally acceptable salt or ester thereof to imazapic of agriculturally acceptable salt or ester thereof is from about 1:4 to about 4:1.

9. The composition of claim 4 wherein the weight ratio of the compound of formula (I) or agriculturally acceptable salt or ester thereof to imazapyr or agriculturally acceptable salt or ester thereof is from about 1:1 to about 8:1.

10. The composition claim 4 wherein the weight ratio of the compound of formula (I) or agriculturally acceptable salt or ester thereof to imazamethabenz-methyl or agriculturally acceptable salt or ester thereof is from about 1:350 to about 1:1.

11. The composition of claim 4 wherein the weight ratio of the compound of formula (I) or agriculturally acceptable salt or ester thereof to imazaquin or agriculturally acceptable salt or ester thereof is from about 1:1 to about 1:8.

12. The composition of claim 1 further comprising an agriculturally acceptable adjuvant or carrier.

13. A method of controlling undesirable vegetation, comprising the steps of:
contacting a plant, wherein the plant is undesirable vegetation or the locus thereof, soil or water, wherein the soil or the water allows for the growth of the undesirable vegetation, with a herbicidally effective amount of a combination comprising (a) a compound of the formula (I):

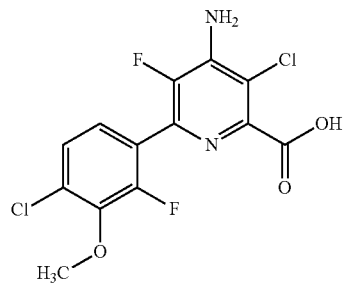

(I)

or a $C_{1-4}$ alkyl ester, or a benzyl ester, or an agriculturally acceptable salt of formula (I): and
(b) an imidazolinone herbicide, wherein (a) and (b) are present in the combination in a ratio such that the combination exhibits synergy for the control of undesirable vegetation, and wherein the undesirable vegetation is controlled in direct seeded, water seeded, or transplanted plants selected from the group of plants consisting of: cereals, wheat, barley, oats, rye, sorghum, and corn/maize.

14. The method of claim 13, wherein the water is part of a flooded rice paddy.

15. The method of claim 13, wherein the (a) and (b) are applied pre-emergently and/or post-emergently to a crop or growing area.

16. The method of claim 13, wherein the undesirable vegetation is controlled in glyphosate-, 5-enolpyruvylshikimate-3-phosphate synthase inhibitor-, glufosinate-, glutamine synthetase inhibitor-, dicamba-, phenoxy auxin-, pyridyloxy auxin-, synthetic auxin-, auxin transport inhibitor-, aryloxyphenoxypropionate-, cyclohexanedione-, phenylpyrazoline-, acetyl CoA carboxylase inhibitor-, imidazolinone-, sulfonylurea-, pyrimidinylthiobenzoate-, triazolopyrimidine-, sulfonylaminocarbonyltriazolinone-, acetolactate synthase or acetohydroxy acid synthase inhibitors-, 4-hydroxyphenyl-pyruvate dioxygenase inhibitor-, phytoene desaturase inhibitor-, carotenoid biosynthesis inhibitor-, protoporphyrinogen oxidase inhibitor-, cellulose biosynthesis inhibitor-, mitosis inhibitor-, microtubule inhibitor-, very long chain fatty acid inhibitor-, fatty acid and lipid biosynthesis inhibitor-, photosystem I inhibitor-, photosystem II inhibitor-, triazine-, or bromoxynil-tolerant crops.

17. The method of claim 13, wherein the undesirable vegetation comprises a herbicide resistant or tolerant plant.

18. The method of claim 17, wherein the resistant or tolerant plant is resistant or tolerant to multiple herbicides.

19. The method of claim 17, wherein the resistant or tolerant plant is resistant or tolerant to acetolactate synthase inhibitors or acetohydroxy acid synthase, photosystem II inhibitors, acetyl CoA carboxylase inhibitors, synthetic auxins, auxin transport inhibitors, photosystem I inhibitors, 5-enolpyruvylshikimate-3-phosphate synthase inhibitors, microtubule assembly inhibitors, fatty acid and lipid biosynthesis inhibitors, protoporphyrinogen oxidase inhibitors, carotenoid biosynthesis inhibitors, long chain fatty acid inhibitors, phytoene desaturase inhibitors, glutamine synthetase inhibitors, 4-hydroxyphenyl-pyruvate-dioxygenase inhibitors, mitosis inhibitors, cellulose biosynthesis inhibitors, herbicides with multiple modes-of-action, quinclorac, arylaminopropionic acids, difenzoquat, endothall, or organoarsenicals.

* * * * *